United States Patent
Cases-Thomas et al.

(10) Patent No.: US 7,354,920 B2
(45) Date of Patent: Apr. 8, 2008

(54) ARYL AND HETEROARYL MORPHOLINE DERIVATIVES

(75) Inventors: Manuel Javier Cases-Thomas, Reading (GB); Helen Louise Haughton, Reading (GB); Robin George Simmonds, Wokingham (GB); Hélène Catherine Eugénie Rudyk, Bracknell (GB); Magnus Wilhelm Walter, Richmond (GB); Sivi Ouwerkerk-Mahadevan, Heverlee (BE); John Joseph Masters, Fishers, IN (US); Carlos Lamas-Peteira, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 473 days.

(21) Appl. No.: 10/524,921

(22) PCT Filed: Aug. 18, 2003

(86) PCT No.: PCT/US03/23270

§ 371 (c)(1), (2), (4) Date: Feb. 15, 2005

(87) PCT Pub. No.: WO2004/018441

PCT Pub. Date: Mar. 4, 2004

(65) Prior Publication Data

US 2006/0003998 A1 Jan. 5, 2006

Related U.S. Application Data

(60) Provisional application No. 60/415,303, filed on Oct. 1, 2002.

(30) Foreign Application Priority Data

Aug. 23, 2002 (GB) .................. 0219687.1

(51) Int. Cl.
*A61K 31/5375* (2006.01)
*C07D 265/30* (2006.01)

(52) U.S. Cl. .................. 514/238.8; 544/106; 544/170; 514/231.2

(58) Field of Classification Search ................ 544/106, 544/170; 514/231.2, 238.8
See application file for complete search history.

(56) References Cited

U.S. PATENT DOCUMENTS 6,274,579 B1 8/2001 Morgan et al.

| | | |
|---|---|---|
| 2006/0035894 A1 | 2/2006 | Walter et al. |
| 2006/0052377 A1 | 3/2006 | Clark et al. |
| 2006/0258654 A1 | 11/2006 | Clark et al. |
| 2007/0060585 A1 | 3/2007 | Gallagher et al. |

FOREIGN PATENT DOCUMENTS

| | | |
|---|---|---|
| EP | 0 721 777 A3 | 7/1996 |
| EP | 0 756 869 A3 | 2/1997 |
| GB | 1 295 447 A | 11/1972 |
| GB | 1 412 546 A | 11/1975 |
| GB | 2 167 407 A | 5/1986 |
| WO | WO 99/15177 | 4/1999 |
| WO | WO 99/64009 | 12/1999 |
| WO | WO 00/39091 | 7/2000 |
| WO | WO 00/50380 | 8/2000 |
| WO | WO 01/01973 A3 | 1/2001 |

OTHER PUBLICATIONS

International Preliminary Examination Report.
International Search Report.
Boot et al. "*Discovery and structure-activity relationships of novel selective norepinephrine and dual serotonin/norepinephrine reuptake inhibitors*", Bioorganic & Medicinal Chemistry Letters, 2005, vol. 15,, pp. 699-703.

*Primary Examiner*—Golam M. M. Shameem
(74) *Attorney, Agent, or Firm*—Charles E. Cohen; Tonya L. Combs; Thomas E. Jackson

(57) ABSTRACT

Compounds of formula (I)

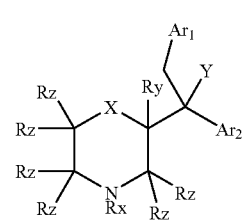

wherein Rx is H; Ry is H or $C_1$-$C_4$ alkyl; each Rz is independently H or $C_1$-$C_4$ alkyl; X represents O; Y represents OH or OR; R is $C_1$-$C_4$ alkyl; and $Ar_1$ and $Ar_2$ are optionally substituted phenyl or 5- or 6-membered heteroaryl rings are selective inhibitors of the reuptake of norepinephrine.

13 Claims, No Drawings

ARYL AND HETEROARYL MORPHOLINE DERIVATIVES

CROSS REFERENCE

This is the national phase application, under 35 USC 371, for PCT/US2003/023270, filed 18 Aug. 2003 which, claims the benefit, under 35 USC 119(e), of GB provisional application 0219687.1, filed 23 Aug. 2002, and U.S. provisional application 60/415,303, filed 01 Oct. 2002.

This invention relates to novel aryl and heteroaryl morpholine compounds, and to their use in selectively inhibiting norepinephrine reuptake.

Selective inhibition of norepinephrine reuptake is a relatively new mode of action for the treatment of affective disorders. Norepinephrine appears to play an important role in the disturbances of vegetative function associated with affective, anxiety and cognitive disorders. Atomoxetine hydrochloride is a selective inhibitor of norepinephrine reuptake, and is marketed for the treatment of attention deficit hyperactivity disorder (ADHD). Reboxetine is also a selective norepinephrine reuptake inhibitor, and is marketed for the treatment of depression. WO99/15177 discloses the use of Reboxetine to treat ADHD and WO01/01973 discloses the use of S,S-Reboxetine to treat ADHD.

According to the present invention there is provided a compound of formula (I)

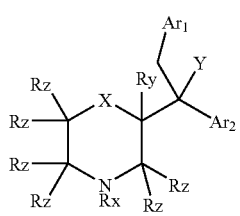

(I)

wherein
Rx is H;
Ry is H or $C_1$-$C_4$ alkyl;
each Rz is independently H or $C_1$-$C_4$ alkyl;
X represents O;
Y represents OH or OR;
R is $C_1$-$C_4$ alkyl;
$Ar_1$ is a phenyl ring or a 5- or 6-membered heteroaryl ring each of which may be substituted with 1, 2, 3, 4 or 5 substituents (depending upon the number of available substitution positions) each independently selected from $C_1$-$C_4$ alkyl, O($C_1$-$C_4$ alkyl), S($C_1$-$C_4$ alkyl), halo, hydroxy, pyridyl, thiophenyl and phenyl optionally substituted with 1, 2, 3, 4 or 5 substituents each independently selected from halo, $C_1$-$C_4$ alkyl, or O($C_1$-$C_4$ alkyl); and
$Ar_2$ is a phenyl ring or a 5- or 6-membered heteroaryl ring each of which may be substituted with 1, 2, 3, 4 or 5 substituents (depending upon the number of available substitution positions) each independently selected from $C_1$-$C_4$ alkyl, O($C_1$-$C_4$ alkyl) and halo;
wherein each above-mentioned $C_1$-$C_4$ alkyl group is optionally substituted with one or more halo atoms;
or a pharmaceutically acceptable salt thereof.

In a preferred embodiment of the present invention, there is provided a compound of formula (I) above wherein:

$Ar_1$ is phenyl, pyridyl, pyrimidyl, thiazolyl, isothiazolyl, oxazolyl, isoxazolyl, thiophenyl, furanyl, imidazolyl, triazolyl, oxadiazolyl or thiadiazolyl, each of which may be substituted with 1, 2, 3, 4 or 5 substituents (depending upon the number of available substitution positions) each independently selected from $C_1$-$C_4$ alkyl, O($C_1$-$C_4$ alkyl), S($C_1$-$C_4$ alkyl), halo, hydroxy, pyridyl, thiophenyl and phenyl optionally substituted with 1, 2, 3, 4 or 5 substituents each independently selected from halo, $C_1$-$C_4$ alkyl, or O($C_1$-$C_4$ alkyl); and
$Ar_2$ is phenyl, pyridyl, pyrimidyl, thiazolyl, isothiazolyl, oxazolyl, isoxazolyl, thiophenyl, furanyl, imidazolyl or triazolyl each of which may be substituted with 1, 2, 3, 4 or 5 substituents (depending upon the number of available substitution positions) each independently selected from $C_1$-$C_4$ alkyl, O($C_1$-$C_4$ alkyl) and halo;
wherein each above-mentioned $C_1$-$C_4$ alkyl group is optionally substituted with one or more halo atoms.

For the compounds of formula (I) above, it is preferred that $Ar_1$ is a phenyl ring or a 5- or 6-membered heteroaryl ring substituted with 1, 2, 3, 4 or 5 substituents, more preferably with 1 or 2 substituents.

For the compounds of formula (I) above, when $Ar_1$ is a substituted phenyl ring or a substituted 5- or 6-membered heteroaryl ring, it is preferred that not more than one of those substituents is a pyridyl, thiophenyl or optionally substituted phenyl group.

Preferred compounds of formula (I) above are those wherein $Ar_1$ includes a substituent attached at the 2-position. That is, the substituent is attached to the atom adjacent to that which forms the point of attachment of $Ar_1$ to the methylene group connecting $Ar_1$ to the rest of the molecule. For example, when $Ar_1$ is phenyl, it is preferably ortho-substituted.

In a further preferred embodiment of the present invention, there is provided a compound of formula (I) above wherein
Rx is H;
Ry is H or $C_1$-$C_4$ alkyl;
each Rz is independently H or $C_1$-$C_4$ alkyl;
X represents O;
Y represents OH or OR;
R is $C_1$-$C_4$ alkyl; and
$Ar_1$ and $Ar_2$ are each independently selected from the group consisting of phenyl, and substituted phenyl; and pharmaceutically acceptable salts thereof.

In this further preferred embodiment, the group $Ar_1$ may be substituted or unsubstituted phenyl. For example, Art may be unsubstituted phenyl or, preferably phenyl substituted with 1, 2, 3, 4 or 5 substituents, preferably with 1 or 2, for example 1, substituent. When disubstituted, the substituted phenyl group is preferably substituted at the 2- and 5-positions. When monosubstituted, the substituted phenyl group is preferably substituted in the 2-position. Suitable substituents include $C_1$-$C_4$ alkyl, O($C_1$-$C_4$ alkyl), S($C_1$-$C_4$ alkyl), halo, and phenyl, optionally substituted with, for example, halo, $C_1$-$C_4$ alkyl, or O($C_1$-$C_4$ alkyl).

In this further preferred embodiment, the group $Ar_2$ may be substituted or unsubstituted phenyl. For example, $Ar_2$ may be phenyl substituted with 1, 2, 3, 4 or 5 substituents, preferably with 1 substituent. Suitable substituents include $C_1$-$C_4$ alkyl, O($C_1$-$C_4$ alkyl), and especially, halo.

"$C_1$-$C_4$ alkyl" as used herein includes straight and branched chain alkyl groups of 1, 2, 3 or 4 carbon atoms, and may be unsubstituted or substituted. $C_1$-$C_2$ alkyl groups are preferred. Suitable substituents include halo, especially Cl and/or F. Thus the term "$C_1$-$C_4$ alkyl" includes haloalkyl. A particularly preferred substituted $C_1$-$C_4$ alkyl group is trifluoromethyl. Similar terms defining different numbers of C atoms (e.g. "$C_1$-$C_3$ alkyl") take an analogous meaning. When Ry is $C_1$-$C_4$ alkyl it is preferably unsubstituted. When Rz is $C_1$-$C_4$ alkyl it is preferably unsubstituted. When R is $C_1$-$C_4$ alkyl it is preferably unsubstituted.

"5-membered heteroaryl ring" as used herein means a 5-membered aromatic ring including at least one heteroatom independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups thiazolyl, isothiazolyl, oxazolyl, isoxazolyl, thiophenyl, furanyl, pyrrolyl, imidazolyl, triazolyl, oxadiazolyl and thiadiazolyl.

"6-membered heteroaryl ring" as used herein means a 6-membered aromatic ring including at least one heteroatom independently selected from N, O and S. Preferably there are not more than three heteroatoms in total in the ring. More preferably there are not more than two heteroatoms in total in the ring. More preferably there is not more than one heteroatom in total in the ring. The term includes, for example, the groups pyridyl, pyrimidyl, pyrazinyl, pyridazinyl and triazinyl.

"Halo" includes P, Cl, Br and I, and is preferably F or Cl.

"Pyridyl" as used herein includes 2-pyridyl, 3-pyridyl and 4-pyridyl.

"Pyrimidyl" as used herein includes 2-pyrimidyl, 4-pyrimidyl and 5-pyrimidyl.

"Pyridazinyl" as used herein includes 3-pyridazinyl and 4-pyridazinyl.

"Pyrazinyl" as used herein includes 2-pyrazinyl and 3-pyrazinyl.

"Triazinyl" as used herein includes 2-(1,3,5-triazinyl), 3-, 5- and 6-(1,2,4-triazinyl) and 4- and 5-(1,2,3-triazinyl).

"Tiazolyl" as used herein includes 2-thiazolyl, 4-thiazolyl and 5-thiazolyl.

"Isothiazolyl" as used herein includes 3-isothiazolyl, 4-isothiazolyl, and 5-isothiazolyl.

"Oxazolyl" as used herein includes 2-oxazolyl, 4-oxazolyl and 5-oxazolyl.

"Isoxazolyl" as used herein includes 3-isoxazolyl, 4-isoxazolyl, and 5-isoxazolyl.

"Thiophenyl" as used herein includes 2-thiophenyl and 3-thiophenyl.

"Furanyl" as used herein includes 2-furanyl and 3-furanyl.

"Pyrrolyl" as used herein includes 2-pyrrolyl and 3-pyrrolyl.

"Imidazolyl" as used herein includes 2-imidazolyl and 4-imidazolyl.

"Triazolyl" as used herein includes 1-triazolyl, 4-triazolyl and 5-triazolyl.

"Oxadiazolyl" as used herein includes 4- and 5-(1,2,3-oxadiazolyl), 3- and 5-(1,2,4-oxadiazolyl), 3-(1,2,5-oxadiazolyl), 2-(1,3,4-oxadiazolyl).

"Thiadiazolyl" as used herein includes 4- and 5-(1,2,3-thiadiazolyl), 3- and 5-(1,2,4-thiadiazolyl), 3-(1,2,5-thiadiazolyl), 2-(1,3,4-thiadiazolyl).

For the compounds of formula (I) above, Ry is preferably H or Me. More preferably Ry is H.

For the compounds of formula (I) above, each Rz is preferably H or Me with 0, 1, 2 or 3 of Rz being Me. More preferably only 1 Rz is Me. Most preferably all Rz are H.

For the compounds of formula (I) above, Y is preferably OH or OMe. More preferably, Y is OH.

For the compounds of formula (I) above, it is preferred that Ry and all Rz are H and Y is OH.

For the compounds of formula (I) above, the preferred stereochemistry is shown below:

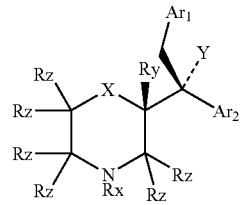

A preferred group of compounds according to the present invention is represented by the formula (II)

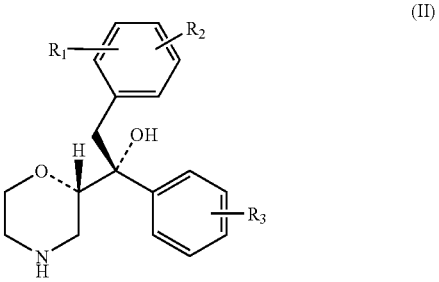

(II)

wherein $R_1$ and $R_2$ are each independently selected from H, $C_1$-$C_4$ alkyl, O($C_1$-$C_4$ alkyl), S($C_1$-$C_4$ alkyl), halo and phenyl; and $R_3$ is selected from H, $C_1$-$C_4$ alkyl and halo; and pharmaceutically acceptable salts thereof.

$R_1$ is preferably $C_1$-$C_3$ alkyl (especially trifluoromethyl), O($C_1$-$C_3$ alkyl) (especially methoxy or trifluoromethoxy), F or phenyl (Ph). $R_2$ is preferably H. $R_2$ is also preferably F. $R_3$ is preferably H.

Especially preferred compounds of the present invention are 1-morpholin-2-yl-1-phenyl-2-(2-trifluoromethoxy-phenyl)-ethanol and 2-(5-fluoro-2-methoxy-phenyl)-1-morpholin-2-yl-1-phenyl-ethanol. For both of these compounds the (S,R) stereoisomer is preferred. For both of these compounds the preferred salt form is the hydrochloride salt.

Compounds of the present invention are selective inhibitors of norepinephrine reuptake. Biogenic amine transporters control the amount of biogenic amine neurotransmitters in the synaptic cleft. Inhibition of the respective transporter leads to a rise in the concentration of that neurotransmitter within the synaptic cleft. Compounds of Formula I and their pharmaceutically acceptable salts preferably exhibit a $K_i$ value less than 500 nM at the norepinephrine transporter as determined using the scintillation proximity assay as described below. More preferred compounds of Formula I and their pharmaceutically acceptable salts exhibit a $K_i$ value less than 100 nM at the norepinephrine transporter. More preferred compounds of Formula I and their pharmaceutically acceptable salts exhibit a $K_i$ value less than 50 nM at the norepinephrine transporter. Especially preferred compounds of Formula I and their pharmaceutically acceptable salts exhibit a $K_i$ value less than 20 nM at the norepinephrine transporter. Preferably, compounds of the present invention selectively inhibit the norepinephrine transporter relative to the serotonin and dopamine transporters by a factor of at least five, more preferably by a factor of at least ten.

In addition, the compounds of the present invention are acid stable. Advantageously, they have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below. They are indicated for the treatment of disorders associated with norepinephrine dysfunction in mammals, especially humans, including children, adolescents and adults.

The term "norepinephrine dysfunction" as used herein refers to a reduction in the amount of norepinephrine neurotransmitter within the synaptic cleft below that which would be considered to be normal or desirable for a species, or an individual within that species. Thus the phrase "disorders associated with norepinephrine dysfunction in mammals" refers to disorders which are associated with a reduction in the amount of norepinephrine neurotransmitter within the synaptic cleft below that which would be considered to be normal or desirable for the mammalian species, or an individual within the species, in question. Some examples of disorders currently believed to be associated with reduced levels of norepinephrine within the synaptic cleft are detailed below.

The compounds of the present invention are also indicated for the treatment of disorders which are ameliorated by an increase in the amount of norepinephrine neurotransmitter within the synaptic cleft of a mammal above that which would be considered to be normal or desirable for the mammalian species, or an individual within the species, in question.

The term "treatment" as used herein refers to both curative and prophylactic treatment of disorders associated with norepinephrine dysfunction.

Compounds of the present invention may be prepared according to the following methods.

A general scheme outlining the synthetic routes to compounds of the present invention wherein Y is OH is shown below (Scheme 1). For clarity, $Ar_2$ is shown as phenyl and Ry and Rz are shown as H. It will be appreciated that analogous methods could be applied for other possible identities of $Ar_2$, Ry and Rz.

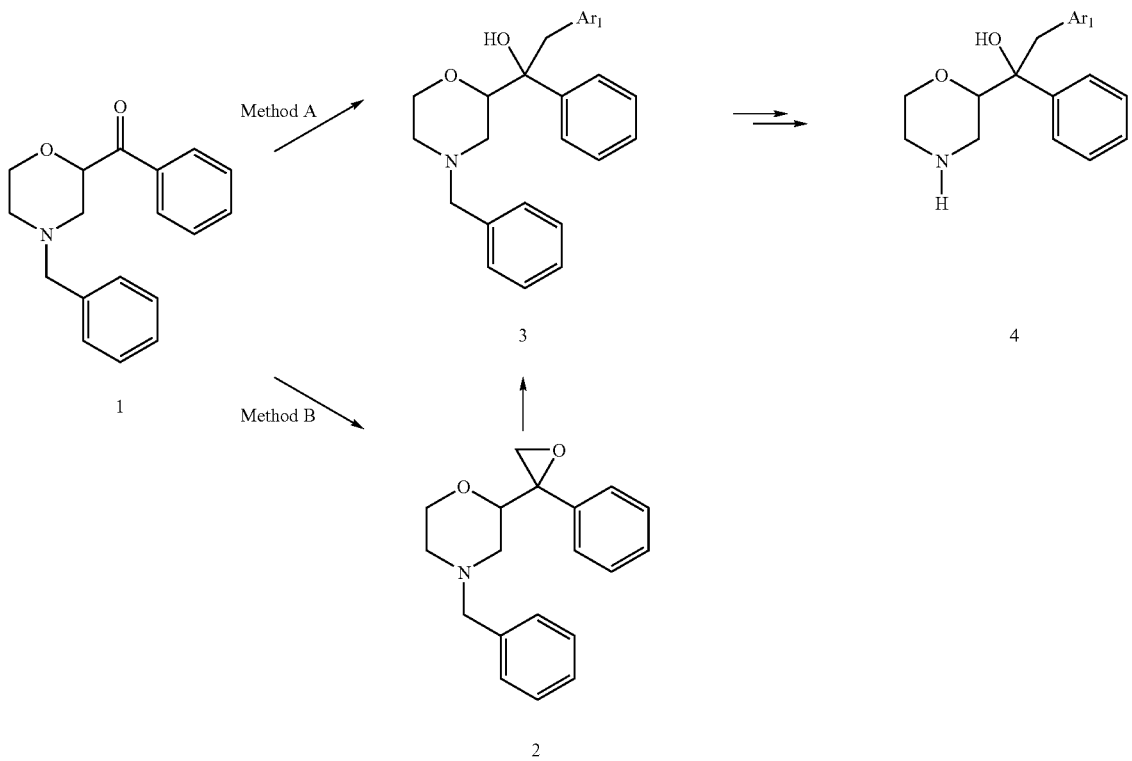

Compounds of the present invention may be prepared by conventional organic chemistry techniques from an N-benzyl-ketomorpholine of type 1 by addition of a suitable organometallic derivative (method A), or via the addition of a suitable organometallic reagent to an epoxide of type 2 (method B), as outlined in Scheme 1.

The racemic intermediates of type 1 may be obtained as outlined in Scheme 2 by condensation of an N-benzyl cyanomorpholine 5 (J. Med. Chem. 1993, 36, pp 683-689) with a suitable aryl organometallic reagent followed by acid hydrolysis. Chiral HPLC separations of the racemic N-benzyl-aryl-ketomorpholine of type 1 gives the required single enantiomer, i.e., the (2S)-N-benzyl-aryl-ketomorpholine of type 6 (Scheme 2).

Scheme 2

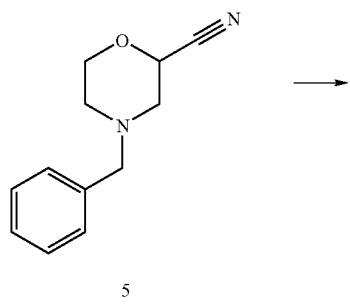

Scheme 3

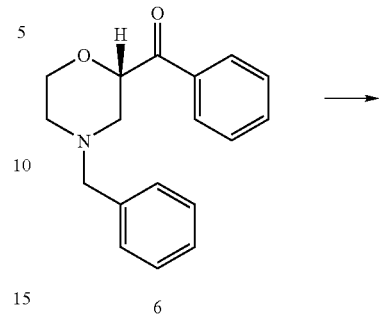

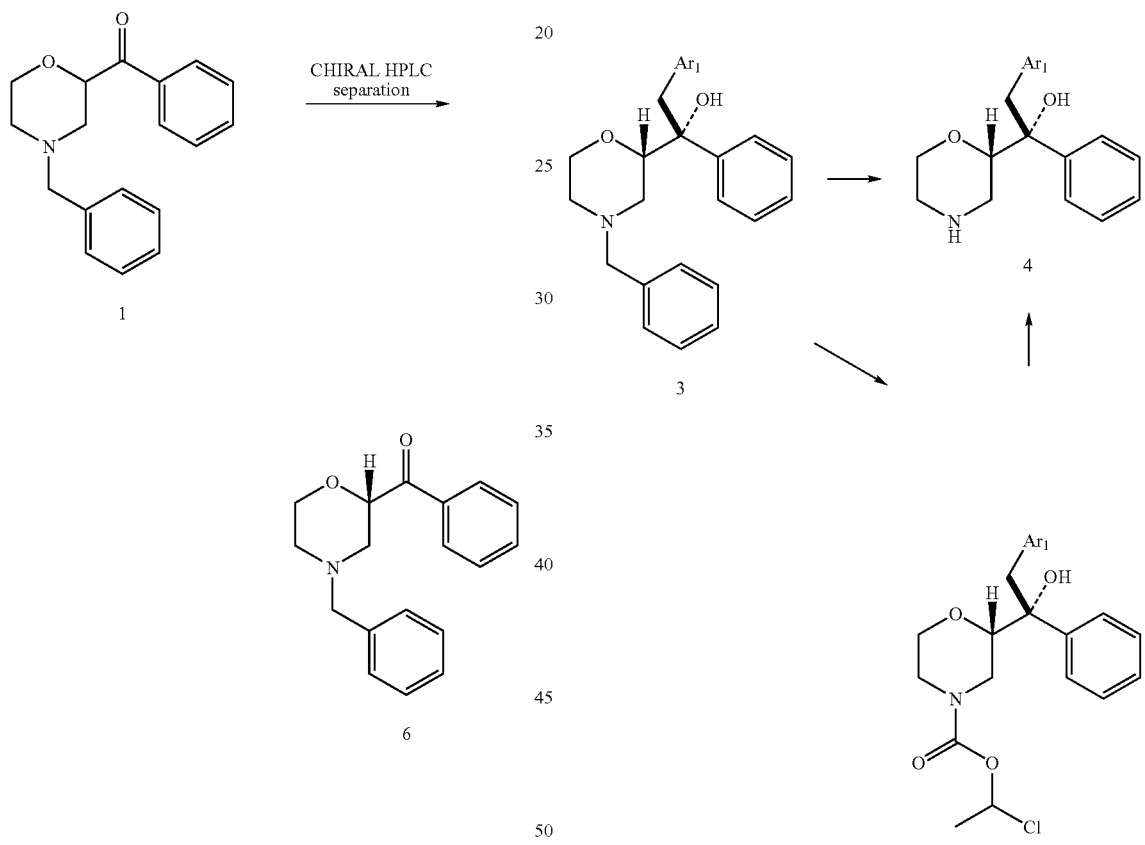

Condensation of a chiral (2S)-N-benzyl-aryl-ketomorpholine of type 6 with a commercially available benzylic magnesium halide or a benzylic magnesium halide prepared using standard Grignard techniques from the corresponding halo-benzylic derivative gives a tertiary alcohol of type 3 without any observed epimerisation of the existing asymmetric center (ee's/de's determinations may be carried out using chiral HPLC) and with very high overall diastereoisomeric excesses (see Scheme 3). The final compounds of type 4 may be obtained after cleavage of the N-benzyl protecting group on a compound of type 3. The deprotection can be done using catalytic palladium hydrogenolysis, or carbamate exchange with ACE-Cl (1-Chloroethyl chloroformate), giving intermediates of type 7, followed by methanolysis as shown in Scheme 3.

The intermediates 3 may be further elaborated using for example organometallic type couplings between an ortho bromide derivative of type 8 and an arylboronic acid as shown in Scheme 4. For clarity, $Ar_1$ and its substituent ($R_1$) are shown as phenyl and substitution occurs at the 2-position. It will be appreciated that analogous methods could be applied for other possible identities of $Ar_1$ and $R_1$ and other possible substitution positions. This approach may also be carried out by solid phase synthetic methods as described in more detail in the specific examples below.

Scheme 4

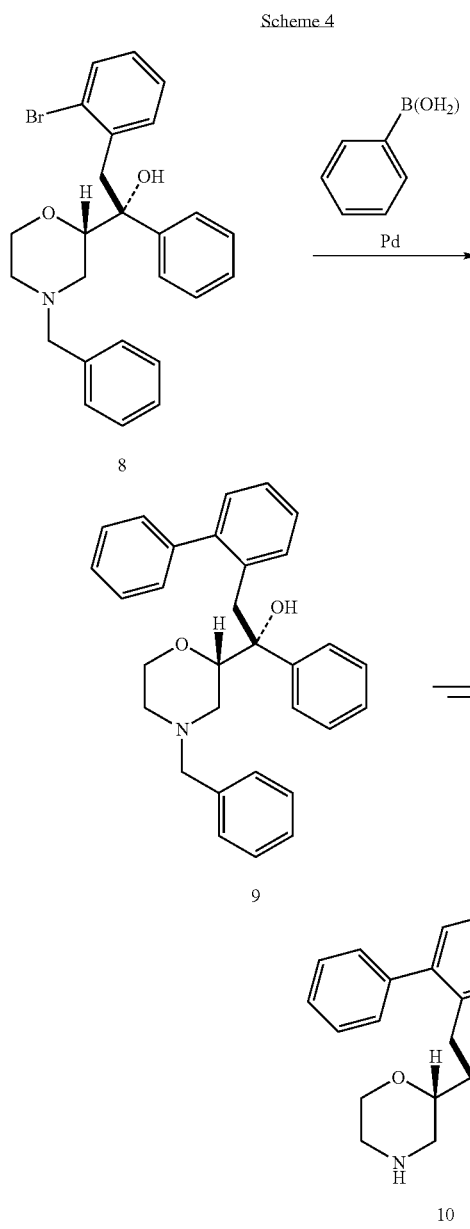

Scheme 5

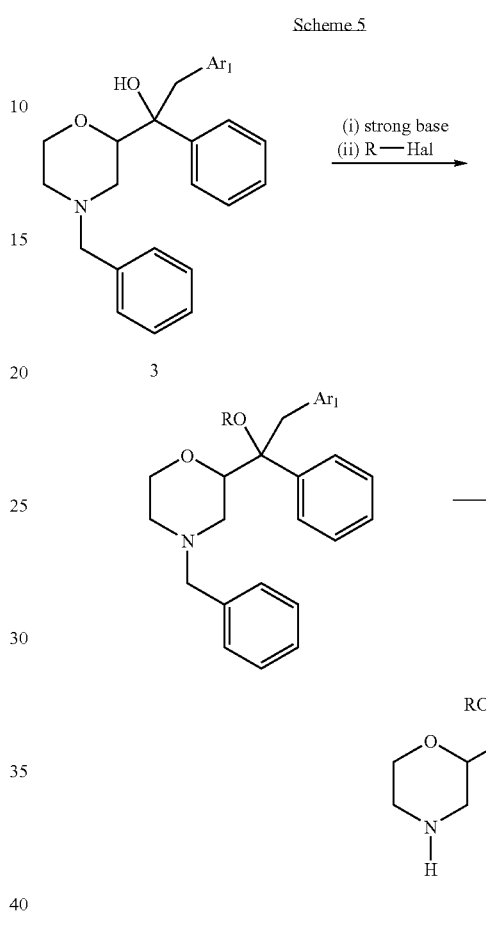

include, for example, sodium hydride. Similarly, suitable alkylating agents will be known to the person skilled in the art and include, for example, $C_1$-$C_4$ alkyl halides such as methyl iodide.

An alternative route for the preparation of the compounds of this invention is method B (see Scheme 1). Formation of the intermediate epoxides of type 2 from racemic N-benzyl-ketomorpholines of type 1, may be done using for example trimethyl sulfoxonium iodide and a suitable base, for example sodium hydride. Condensation of 2 with a commercially available aryl organometallic, or an aryl organometallic prepared from the corresponding halo aryl derivative, gives the intermediates of type 3, as mixtures of diastereoisomers. Final deprotections may be done as described above (see scheme 3). Final compounds made using method B may be purified using chiral HPLC.

Compounds of the present invention wherein Y is OR and R is $C_1$-$C_4$ alkyl, may be synthesized by standard alkylation of intermediates of type 3 prior to deprotection of the morpholine N-atom as shown in Scheme 5. Suitable strong bases will be known to the person skilled in the art and In another embodiment of the present invention there is provided a process for the preparation of compounds of formula (I) comprising the step of deprotecting a compound of the formula (III)

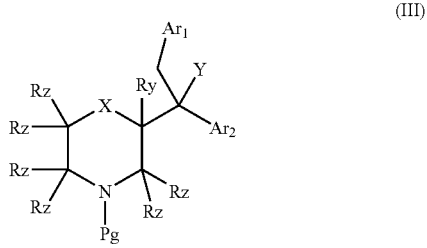

(III)

wherein Pg represents an N-protecting group and all other variables are as defined for formula (I), to provide a compound of formula (I), optionally followed by the step of forming a pharmaceutically acceptable salt.

In another embodiment of the present invention there are provided intermediates useful for the preparation of compounds of formula (I). Thus the present invention provides a compound of formula (IV)

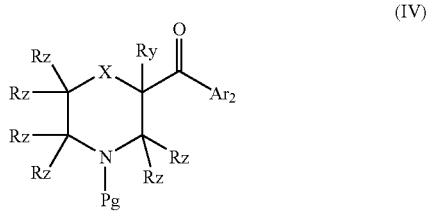

wherein Pg represents an N-protecting group and all other variables are as defined for formula (I).

For the intermediates of formula (IV) above, the preferred stereochemistry is shown below:

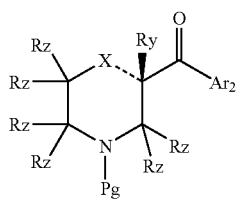

Preferred intermediates include the compounds

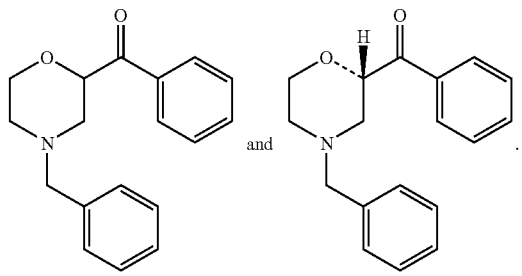

Suitable N-protecting groups will be known to the person skilled in the art as will methods for their removal. Further information on suitable deprotecting groups is contained in the well known text "Protective Groups in Organic Synthesis", Theodora W. Greene and Peter G. M. Wuts, John Wiley & Sons, Inc., New York, 1999, pp. 494-653. Preferred N-protecting groups include benzyl, allyl, carbamates such as benzyloxycarbonyl (cbz) and t-butyloxycarbonyl (boc) and amides.

In addition to the compounds of formula (I) and formula (II), and processes for the preparation of said compounds, the present invention further provides pharmaceutical compositions comprising a compound of formula (I) or formula (II) or a pharmaceutically acceptable salt thereof, together with a pharmaceutically acceptable diluent or carrier.

Further, the present invention provides a compound of formula (I) or formula (II) or a pharmaceutically acceptable salt thereof, for use as a pharmaceutical; and a compound of formula (I) or formula (II) or a pharmaceutically acceptable salt thereof, for use as a selective inhibitor of the reuptake of norepinephrine.

The present compounds and salts can be employed in the treatment of disorders associated with norepinephrine dysfunction in mammals, including affective, anxiety, and cognitive disorders.

Disorders associated with norepinephrine dysfunction in mammals include, for example, nervous system conditions selected from the group consisting of an addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, anorexia nervosa, apathy, an attention-deficit disorder (ADD) due to general medical conditions, attention-deficit hyperactivity disorder (ADHD) including the predominantly inattentive type of ADHD and the predominantly hyperactive-impulsive type of ADHD, bipolar disorder, bulimia nervosa, chronic fatigue syndrome, chronic or acute stress, cognitive disorders including mild cognitive impairment (MCI) and cognitive impairment associated with schizophrenia (CIAS), conduct disorder, cyclothymic disorder, dementia of the Alzheimers type (DAT), depression (including adolescent depression and minor depression), dysthymic disorder, emotional dysregulation, fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hypotensive states including orthostatic hypotension, incontinence (i.e., stress incontinence, genuine stress incontinence, and mixed incontinence), an inhalation disorder, an intoxication disorder, mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, peripheral neuropathy, post-traumatic stress disorder, premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia. The compounds of the present invention are particularly suitable for the treatment of attention deficit hyperactivity disorder, ADHD. The compounds of the present invention are also particularly suitable for the treatment of schizophrenia.

Thus, the present invention also provides a compound of formula (I) or formula (II) or a pharmaceutically acceptable salt thereof for selectively inhibiting the reuptake of norepinephrine. Preferably such selective inhibition occurs within mammalian cells (including mammalian cell membrane preparations), especially those found within the central and/or peripheral nervous system. More preferably such selective inhibition occurs within the cells of the central nervous system of a mammal, especially a human, in need thereof; and a compound of formula (I) or formula (II) or a pharmaceutically acceptable salt thereof for treating disorders associated with norepinephrine dysfunction in mammals; and the use of a compound of formula (I) or formula (II), or a pharmaceutically acceptable salt thereof, in the manufacture of a medicament for selectively inhibiting the reuptake of norepinephrine; and the use of a compound of formula (I) or formula (II), or a pharmaceutically acceptable salt thereof, in the manufacture of a medicament for the treatment of disorders associated with norepinephrine dysfunction in mammals, including the disorders listed herein.

Further, the present invention provides a method for selectively inhibiting the reuptake of norepinephrine in mammals, comprising administering to a patient in need thereof an effective amount of a compound of formula (I) or formula (II) or a pharmaceutically acceptable salt thereof; and a method for treating disorders associated with norepinephrine dysfunction in mammals, comprising administering to a patient in need thereof an effective amount of a compound of formula (I) or formula (II) or a pharmaceutically acceptable salt thereof.

The present invention includes the pharmaceutically acceptable salts of the compounds of formula (I) and formula (II). Suitable salts include acid addition salts, including salts formed with inorganic acids, for example hydrochloric, hydrobromic, nitric, sulphuric or phosphoric acids, or with organic acids, such as organic carboxylic or organic sulphonic acids, for example, acetoxybenzoic, citric, glycolic, o-mandelic-l, mandelic-dl, mandelic d, maleic, mesotartaric monohydrate, hydroxymaleic, fumaric, lactobionic, malic, methanesulphonic, napsylic, naphthalenedisulfonic, naphtoic, oxalic, palmitic, phenylacetic, propionic, pyridyl hydroxy pyruvic, salicylic, stearic, succinic, sulfanilic, tartaric, 2-hydroxyethane sulphonic, toluene-p-sulphonic, and xinafoic acids.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that compounds of formula (I) and formula (II) possess one or more asymmetric carbon atoms, and that in the present invention specific individual stereoisomers are preferred. In the present specification, where a structural formula does not specify the stereochemistry at one or more chiral centres, it encompasses all possible stereoisomers and all possible mixtures of stereoisomers (including, but not limited to, racemic mixtures), which may result from stereoisomerism at each of the one or more chiral centers.

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent, excipient or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosols (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propyl-hydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage unit containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

The following examples illustrate compounds of the present invention and methods for their preparation.

Stereochemical Conventions

The absolute stereochemistry of the compound below was determined using X-ray crystallography.

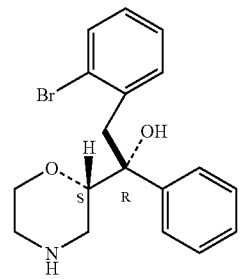

All final compounds were obtained as single isomers either through the use of chirally pure starting materials or chiral separation methods, such as chiral Synthesis of Intermediates.

Preparation of
(4-Benzyl-morpholin-2-yl)-phenyl-methanone a) 4-Benzyl-morpholine-2-carbonitrile

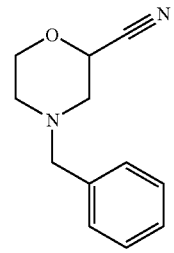

A one-litre reactor with mechanical stirring, cooled by an ice bath, was charged with N-benzylethanolamine (172.2 g; 1 equiv. available from Aldrich Chemical Company). 2-Chloroacrylonitrile (100 g; 1 equiv. available from Aldrich Chemical Company) was added dropwise over 2 minutes. The temperature was maintained between 23° C. and 29° C. by means of the ice bath and subsequently a water bath at 15° C. N-Benzylethanolamine was still detected on TLC after 4.5 h stirring. After one night stirring at room temperature (water bath), no N-benzylethanolamine was detectable by $^1$H NMR. The mixture was dissolved in tetrahydrofuran and transferred to a 2 L reactor cooled to −5° C. by ice/NaCl bath. The total volume of tetrahydrofuran was 1.35 L. Potassium tert-butoxide (148 g; 1.1 equiv.) was added by portions in 1 hour, keeping the reaction temperature at 0±2° C. After 1 hour post-stirring at 0° C., the mixture was quenched with saturated NaHCO$_3$ (500 mL). The aqueous layer was extracted with diethyl ether (500 mL). Organic layers were dried on MgSO$_4$ and evaporated to dryness. The title compound (149.8 g; 65%) was obtained after percolation of the 250 g dry residue on 1 kg of SiO$_2$, eluting with the following gradient:

| | |
|---|---|
| 5% AcOEt - 95% n-heptane | 2.5 L |
| 10% AcOEt - 90% n-heptane | 2 L |
| 15% AcOEt - 85% n-heptane | 2 L |
| 20% AcOEt - 80% n-heptane | 5 L | b) (2S)-(4-Benzyl-morpholin-2-yl)-phenyl-methanone

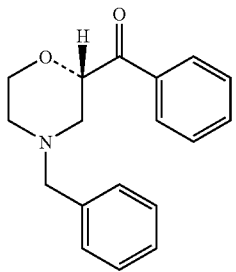

A 3 l double jacket reactor was charged with 4-Benzyl-morpholine-2-carbonitrile (135.05 g; 1 eq) and dry diethyl ether (1.4 l). Alternatively, toluene may be used in place of diethyl ether. When Tj=0° C. and Tm=1° C. (Tj=temperature of the jacket, Tm=temperature of the mass), phenyl magnesium chloride (2M sol. in tetrahydrofuran, 360 ml, 1.08 equiv., available from Aldrich Chemical Company) was added dropwise over 1 hour. Tm rose to 4° C. and came back to 2° C. at the end of the addition. Tm was progressively raised to 17.5° C. over 45 minutes and the mixture stirred at this temperature for another 45 minutes. The reactor was cooled down to Tm=2° C. and Tj=0° C. (75 minutes) and hydrochloric acid (700 ml of 5N solution) was added in two portions. Tm rose to 33° C. After some minutes, the hydrochloride salt of the ketone crystallised. When Tm=Tj=room temperature, the triphasic suspension was filtered. The organic layer of the mother liquors was eliminated. The filtration cake was then washed with methylene chloride (700 ml). This liquor was charged in the reactor with the acid aqueous layer. Treatment of the hydrochloride salt: After drying under vacuum, 164.4 g of the hydrochloride contaminated with MgCl$_2$ were suspended in a biphasic mixture of water/methylenechloride (500 ml/800 ml). The suspension was basified with aqueous sodium hydroxide (75 ml of a 30% solution) under ice bath cooling. Mg(OH)$_2$ precipitated and the aqueous layer was extracted with methylene chloride. The organic layers were filtered on a bed of Celite 512 after addition of Celite. The filtered organic phase was dried over magnesium sulphate and evaporated to dryness. The ketone crystallized readily on standing (132.4 g; 70%). Treatment of the mother liquors: The combined organic phases were washed with aqueous sodium hydroxide (750 ml of a 2N solution). Celite 512 (160 g) was added to the suspension which was then filtrated through a bed of Celite. The aqueous layer was separated and extracted with methylene chloride. The combined organic phases were dried over magnesium sulphate and evaporated to dryness to provide 35.8 g of the title compound enriched with unreacted nitrile. Chiral compound was obtained after separation using chiral HPLC on a Daicel chiralpak AD 20 µm column with 100% Ethanol/0.3% DMEA as eluent at a flow rate of 150 ml/min and UV-detection at 300 nm. Alternatively, the two enantiomers may be separated by fractional crystallization from acetonitrile using from 0.55 to 1 equivalent of dibenzoyltartaric acid to generate diastereoisomeric salts of the title compound. The crystals may be collected by filtration and neutralized with 30% NaOH to afford the optically enriched title compound.

Preparation of (4-Benzyl-morpholin-2-yl)-phenyl-methanone—One pot synthesis

A 1600 L GL reactor under N$_2$ was successively loaded with 2-chloroacrylonitrile (33.2 kg, 379 moles) and toluene (114 L) at 21° C. Then, N-benzylethanolamine (57 kg, 377 moles) was added and the reaction mixture was post-agitated at room temperature for about 17 h. Then, the mixture was diluted with toluene (336 L), cooled down to −12.4° C. and potassium t-butoxide (42.3 kg, 377 moles) was added in portions (10) maintaining −13.7° C.≦Tmass≦−2.8° C. The mixture was post-agitated at about 0° C. for 2.5 h, quenched by adding ultra pure water (142.5 L) maintaining 2.1° C.≦Tmass≦8.7° C. The aqueous layer (176 kg) was separated after 35 minutes of post-stirring allowing the mixture to reach 15° C. and the toluene layer was washed with ultra pure water (142.5 L) and the aqueous layer (162 kg) was separated. The organic layer was then concentrated under reduced pressure (150 mbars) maintaining Tmass≦60° C. in order to distill 162 kg of toluene. The filtrates were then diluted with toluene (114 L) and treated with SiO$_2$ (Merck silica gel 60, 0.063-0.1 mm, 74.1 kg) under agitation at room temperature for 1.25 h. SiO$_2$ was filtered and rinsed with toluene (2×114 L). Then, the filtrates were concentrated under reduced pressure (150 mbars) maintaining Tmass≦60° C. in order to distill 351.8 kg of toluene (KF: 0.01% w/w H$_2$O).

The solution of 4-Benzyl-morpholine-2-carbonitrile (169.2 kg) was diluted with toluene (157 L) and was cooled to 0° C. and phenylmagnesiumchloride (25 wt. % solution in THF, 213 kg, 389 moles, 1.36 molar equiv.) was slowly added (over 3.5 h) to the reaction mixture, maintaining the temperature at −3° C.≦Tmass≦7° C. The reaction mixture was post-stirred for 2 hours at Tmass≈0° C. Then, the quench was performed by adding acetic acid (8.55 L, Tmass=5→17.2° C.), post stirring 10 minutes and cooling to 5° C. before adding an acetic acid/water mixture (229 L, 33/67 v/v). During the quench, addition was performed at such a rate that Tmass did not exceed 20° C. (typical Tmass=4.6° C. to 10.4° C.). The mixture was post-agitated overnight at RT and the aqueous layer (285.8 kg) was extracted.

The toluene layer was cooled to 0° C. and a 5 N NaOH aqueous solution (420.1 kg) was slowly added maintaining the temperature at −2.4° C.≦Tmass≦11° C. The reaction mixture was post-stirred for 1 h and the aqueous layer (494.8 kg) was extracted. The toluene layer was concentrated under reduced pressure (50 mbars) maintaining Tmass≦60° C. in order to distill 356.2 kg of toluene and isopropanol (180.4 kg) was added. The toluene was stripped off under reduced pressure (100 mbars) maintaining Tmass≦60° C. in order to distill 186.4 kg of toluene and isopropanol (135 kg) was added again to the mixture. A last distillation of toluene was performed under reduced pressure (50 mbars) maintaining Tmass≦60° C. in order to distill 131 kg of toluene and isopropanol (49.4 kg) was finally added to the mixture and the solution was stirred at RT until crystallization (17 minutes).

Ultra pure water was added (125.4 L) and the mixture was stirred overnight at RT and cooled down to about 0° C. for 1 hour. The precipitate was filtered and rinsed with a cooled water/isopropanol 50/50 v/v solution (76.6 kg). The wet precipitate was dried under vacuum at Tjack=35° C. for 96 hours to obtain the title compound as an off-white powder with 59% overall yield. The title compound may be resolved by the fractional crystallisation process described above.

Preparation of (4-Benzyl-morpholin-2-yl)-(3-fluoro-phenyl)-methanone a) (4-Benzyl-morpholin-2-yl)-(3-fluoro-phenyl)-methanone

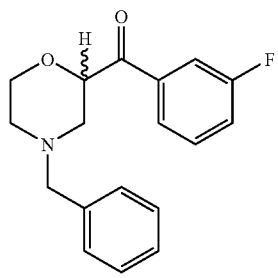

To a solution of 4-Benzyl-morpholine-2-carbonitrile (10 g, 50 mmol) in dry diethyl ether (100 ml) at −10° C. under an atmosphere of nitrogen was added (time of addition 30 minutes) a solution of 3-fluorophenylmagnesium bromide (0.5N solution in tetrahydrofuran, 120 ml, 60 mmol, 1.2 equivalents, available from Aldrich Chemical Company or Rieke Metals) and the reaction mixture was further stirred at −10° C. for 30 minutes. Then the reaction was allowed to warm to room temperature and stirred for one hour. The reaction was then cooled to 0° C. and quenched by addition of hydrochloric acid (2N aqueous solution, 50 ml) and the resulting mixture was stirred for 30 minutes at 0° C. Then the solution was concentrated in vacuo and the residue was taken-up by sodium hydroxide (2N aqueous solution, 60 ml). The aqueous solution was extracted with diethyl ether, the organics fractions were collected and dried ($MgSO_4$) and the solvent removed under reduced pressure to give the title compound as a brown oil (15 g, 100%). FIA [M+H]+=300.1.

Preparation of 2-Chloromethyl-4-fluoro-1-methoxy-benzene a) (5-Fluoro-2-methoxy-phenyl)-methanol

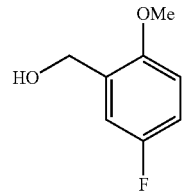

To a solution of 2-Methoxy-5-fluorobenzaldehyde (11.093 g, 1 equiv.-available from Aldrich Chemical Company) in methanol at −10° C. under nitrogen atmosphere was added $NaBH_4$ (7.515 g, 2.7 equiv.) portionwise. The solution was allowed to warm to room temperature and after 30 minutes the reaction solvent was removed under reduced pressure and replaced with dichloromethane. This solution was poured onto ice water and further extracted with dichloromethane. The organic fractions were collected and dried ($MgSO_4$) and the solvent removed under reduced pressure to give the title compound as an oil (9.794 g, 87%). $^1$H NMR (300 MHz, $CDCl_3$): δ 2.58 (m, 1H), 3.81 (s, 3H), 4.63 (d, 2H, J=6.3 Hz), 6.78 (dd, 1H, J=8.9 and 4.3 Hz), 6.94 (td, 1H, J=8.5 and 3.1 Hz), 7.04 (dd, 1H, J=8.7 and 3.1 Hz).

b) 2-Chloromethyl-4-fluoro-1-methoxy-benzene

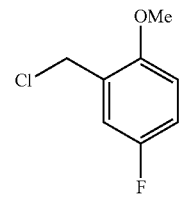

Neat (5-Fluoro-2-methoxy-phenyl)-methanol (19.587 g, 1 equiv.) was added to neat $SOCl_2$ (42.2 mL, 4.6 equiv.) at −78° C. under a nitrogen atmosphere and the solution was then allowed to warm to room temperature and stirred until evolution of gas had ceased. An equivalent volume of anhydrous toluene was added to the flask and the solution heated to 60° C. On cooling the reaction solution was poured onto ice water. The toluene layer was separated and dried ($MgSO_4$) and the solvent removed under reduced pressure. The crude material was sublimed (60-80° C./0.05 mBarr) to give the title compound as a white solid (13.40 g, 61%). $^1$H NMR (300 MHz, $CDCl_3$): δ 3.87 (s, 3H), 4.60 (s, 2H), 6.79-7.20 (m, 3H).

Preparation of 1-Chloromethyl-2-isopropoxy-benzene a) (2-Isopropoxy-phenyl)-methanol

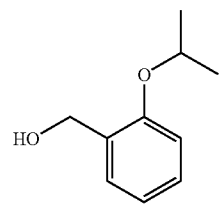

A mixture of 2-hydroxybenzyl alcohol (21.04 g, 1 equiv., available from Aldrich Chemical Company), 2-isopropyl iodide (32.3 mL, 1.9 equiv., available from Aldrich Chemical Company) and $K_2CO_3$ (71.42 g, 3 equiv.) in ethanol was refluxed for 3 hours. On cooling the reaction mixture was filtered and the solvent removed under reduced pressure and replaced with dichloromethane, and then filtered and the solvent removed to give the title compound as an oil (27.751 g, 99%). $^1$H NMR (300 MHz, $CDCl_3$): δ 1.37 (d, 6H, J=6.0 Hz), 3.55 (bs, 1H), 4.50-4.70 (m, 3H), 6.78-6.90 (m, 2H), 7.15-7.25 (m, 2H).

b) 1-Chloromethyl-2-isopropoxy-benzene

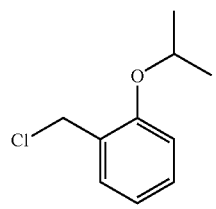

The title compound was prepared using the general procedure outlined above for the preparation of 2-Chloromethyl fluoro-1-methoxy-benzene followed by the following treatment:

The crude reaction material was chromatographed on silica gel and eluted 1:9 ethyl acetate/heptane prior to distillation (40-60° C./0.05 mBar). $^1$H NMR (300 MHz, $CDCl_3$): δ 1.37 (d, 6H, J=6.0 Hz), 4.50-4.70 (m, 3H), 6.80-7.00 (m, 2H), 7.23-7.30 (m, 2H).

Synthesis of Compounds of the Invention.

EXAMPLE 1

Preparation of (S,R)-2-(2-Methoxy-phenyl)-1-morpholin-2-yl-1-phenyl-ethanol hydrochloride a) 1-(4-Benzyl-morpholin-2-yl)-2-(2-methoxy-phenyl)-1-phenyl-ethanol

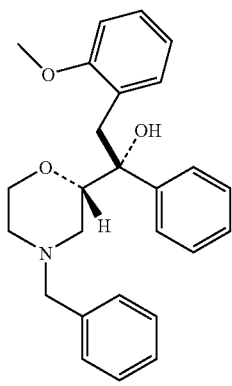

Solid magnesium turnings (9.5 g, 28 equiv.) under nitrogen atmosphere at room temperature were stirred vigorously with a magnetic stirring bar overnight. The magnesium was then covered with dry diethyl ether and to the suspension was added 1,2-dibromoethane (50 μL). A cold bath was then applied followed by dropwise addition of 1-chloromethyl-2-methoxy-benzene (18.18 g, 5 equiv. available from Aldrich Chemical Company) in diethyl ether (71 mL) which maintained the temperature at up to 15° C. The resulting black suspension was stirred at room temperature for 30 minutes and cooled down at −20° C. A solution of (4-Benzyl-morpholin-2-yl)-phenyl-methanone (4 g, 1 equiv.) in diethyl ether (50 mL) was then added dropwise via canula. The reaction mixture was left to warm to room temperature over two hours and then quenched by addition of aqueous saturated solution of $NaHCO_3$ (50 mL). The aqueous solution was extracted with diethyl ether, the organic phase dried with $MgSO_4$, evaporated in vacuo to give 7 g of a yellow amorphous solid. The compound was taken without further purification in the next step. FIA $[M+H]^+=404$.

b) 2-(2-Methoxy-phenyl)-1-morpholin-2-yl-1-phenyl-ethanol hydrochloride

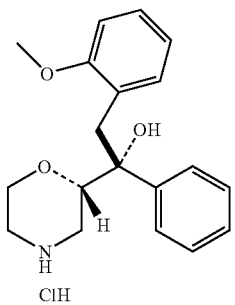

To a solution of 1-(4-Benzyl-morpholin-2-yl)-2-(2-methoxy-phenyl)-1-phenyl-ethanol (1 g, 1 equiv.) in ethyl acetate (100 mL) at room temperature under nitrogen atmosphere was added ammonium formate (3.9 g, 25 equiv.) followed by addition of palladium on charcoal (10%, 1 g.). The reaction mixture was heated to reflux for 1 hour, cooled to room temperature and then filtered through Celite. All volatiles were evaporated under vacuum, and the resulting solid was purified via preparative HPLC. The isolated white solid was taken up in ethanol. Hydrogen chloride was added (large excess of 2M solution in diethyl ether) and the mixture was stirred until it became a clear solution. Then all the volatiles were evaporated in vacuo, to give 650 mg of the title compound as white solid (75%). $^1$H NMR (300 MHz, DMSO D6) δ: 2.43-2.51 (m, 2H), 2.77-2.92 (m, 2H), 3.15-3.23 (m, 3H), 3.41 (s, 3H), 4.10-4.19 (m, 2H), 6.66-6.72 (m, 2l), 6.98-7.07 (m, 2H), 7.13-7.20 (m, 5H), 9.32 (bs, 2H). LCMS (12 minute method) $[M+H]^+=314$ @ Rt 3.96 min. single major peak.

EXAMPLE 2

Preparation of (S,R) 2-(2-Ethoxyl-phenyl)-1-morpholin-2-yl-1-phenyl-ethanol hydrochloride a) 1-(4-Benzyl-morpholin-2-yl)-2-(2-ethoxy-phenyl)-1-phenyl-ethanol

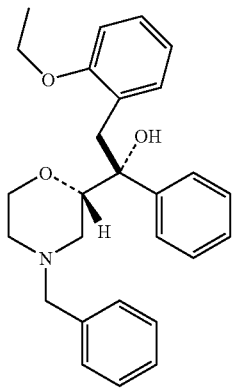

The procedure for the synthesis of example 1a, 1-(4-Benzyl-morpholin-2-yl)-2-(2-methoxy-phenyl)-1-phenyl-ethanol, was followed using commercially available 2-ethoxybenzylmagnesium bromide (available from Rieke-Metals) as starting material and making non-critical variations, to yield the title compound. FIA [M+H]$^+$=418.

b) 2-(2-Ethoxy-phenyl)-1-morpholin-2-yl-1-phenyl-ethanol hydrochloride

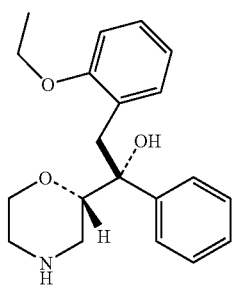

The procedure for the synthesis of example 1b, 2-(2-Methoxy-phenyl)-1-morpholin-2-yl-1-phenyl-ethanol hydrochloride was followed making non-critical variations, to yield the title compound. $^1$H NMR (300 MHz, DMSO D6) δ: 1.11 (t, 3H, J=6.97 Hz), 2.43-2.56 (m, 1H), 2.81-2.96 (m, 2H), 3.17-3.27 (m, 3H), 3.55-3.67 (m, 2H), 3.84-3.92 (m, 1H), 4.05-4.20 (m, 2H), 6.68-6.74 (m, 2H), 7.01-7.18 (m, 8H), 8.92 (bs, 2H) ppm. LCMS (12 minute method) [M+H]$^+$ =328 @ Rt 4.57 min. single major peak.

EXAMPLE 3

Preparation of (S,R) 2-(2-Isopropoxy-phenyl)-1-morpholin-2-yl-1-henyl-ethanol hydrochloride a) 1-(4-Benzyl-morpholin-2-yl)-2-(2-isopropoxy-phenyl)-1-phenyl-ethanol

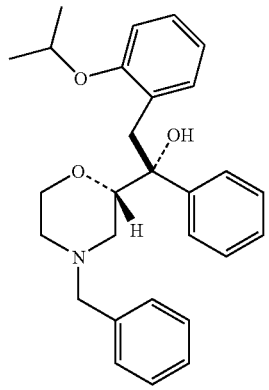

Solid magnesium turnings (4.6 g, 48 equiv.) under nitrogen atmosphere at room temperature were stirred vigorously with a magnetic stirring bar overnight. The magnesium was then covered with dry tetrahydrofuran. A cold bath was then applied followed by dropwise addition of 1-chloromethyl-2-isopropoxy-benzene (3.0 g, 4 equiv. prepared as described above) in tetrahydrofuran (40 mL). During slow addition of the electrophile no exotherm was observed so on completion of addition 3 crystals of Iodine were added to promote initiation of the reaction. After this addition the reaction temperature was allowed to spike to 50° C. then cooled rapidly to 8° C. before being left to warm to room temperature for one hour. The resulting black suspension was cooled down to −10° C. and a solution of (4-Benzyl-morpholin-2-yl)-phenyl-methanone (1.2 g, 1 equiv.) in tetrahydrofuran (10 mL) was then added dropwise. The reaction mixture was left to warm to room temperature over thirty minutes and then quenched by addition of aqueous saturated solution of NaHCO$_3$ (50 mL) prior to filtration through Celite. The aqueous solution was extracted with diethyl ether, the organic phase dried with MgSO$_4$, evaporated in vacuo to give 3 g of a yellow amorphous solid. The compound was taken without further purification in the next step. LCMS (6 minutes method) [M+H]$^+$=432 @ Rt 3.25 min. major peak.

b) 2-(2-Isopropoxy-phenyl)-1-morpholin-2-yl-1-phenyl-ethanol hydrochloride

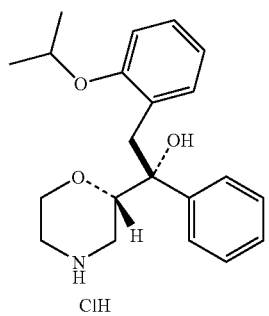

The procedure for the synthesis of example 1b, 2-(2-Methoxy-phenyl)-1-morpholin-2-yl-1-phenyl-ethanol hydrochloride was followed making non-critical variations, to yield the title compound. ¹H NMR (300 MHz, MeOH D3) δ: 1.12-1.16 (m, 6H), 2.51-2.55 (m, 1H), 2.89-3.14 (m, 4H), 3.56-3.60 (m, 1H), 3.82-3.92 (m, 1H), 3.99-4.03 (m, 1H), 4.17-4.22 (m, 1H), 4.36-4.44 (m, 1H), 6.50-6.55 (m, 1H), 6.66-6.73 (m, 2H), 6.92-6.98 (m, 1), 7.07-7.20 (m, 5H) ppm. LCMS (12 minutes method) [M+H]⁺=342 @ Rt 4.90 min. major peak.

EXAMPLE 4

Preparation of (S,R) 1-(3-Fluoro-phenyl)-2-(2-methoxy-phenyl)-1-morpholin-2-yl-ethanol hydrochloride a) 1-(4-Benzyl-morpholin-2-yl)-1-(3-fluoro-phenyl)-2-(2-methoxy-phenyl)-ethanol

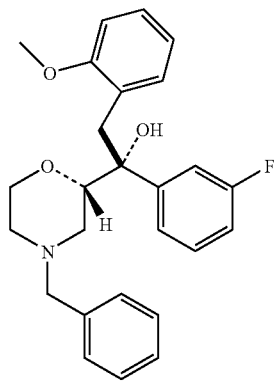

A magnetically stirred 0.25M tetrahydrofuran solution of commercially available 2-methoxybenzylmagnesium bromide (available from Rieke-Metals) (80 ml, 3 equiv.) under nitrogen atmosphere was cooled to −10° C. and to this was added neat (4-Benzyl-morpholin-2-yl)-1-(3-fluoro-phenyl)-methanone (2.1 g, 1 equiv.). The solution was allowed to warm to room temperature and reaction progress followed using mass spectrometry. After 1.5 hours 2-methoxybenzylmagnesium bromide solution (14 ml, 0.5 equiv.) was again added to the reaction and after a further 0.5 hours an aqueous saturated solution of NaHCO₃ (50 mL) was added to halt the reaction. The aqueous solution was extracted with diethyl ether, the organic phase dried with MgSO₄, evaporated in vacuo to give 2.8 g of a yellow amorphous solid. The compound was taken without further purification in the next step. LCMS (6 minutes method) [M+H]⁺=422 @ Rt 3.03 and 2.86 min. major peaks.

b) (S,R)-1-(3-Fluoro-phenyl)-2-(2-methoxy-phenyl)-1-morpholin-2-yl-ethanol hydrochloride

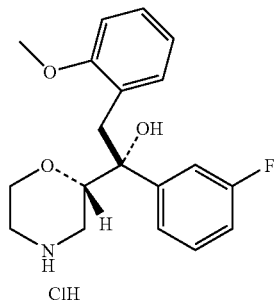

To a solution of 1-(4-Benzyl-morpholin-2-yl)-1-(3-fluoro-phenyl)-2-(2-methoxy-phenyl)-ethanol (2.8 g, 1 equiv.) in ethyl acetate (100 mL) at room temperature under nitrogen atmosphere was added ammonium formate (4.3 g, 10 equiv.) followed by addition of palladium on charcoal (10%, 2.7 g.). The reaction mixture was heated to reflux for 1 hour, cooled to room temperature and then filtered through Celite. All volatiles were evaporated under vacuum, and the resulting solid was purified via preparative HPLC to give the desired diastereoisomers. The active enantiomer was obtained after a further preparative chiral HPLC separation. The active enantiomer, a white solid, was next taken up in ethanol and hydrogen chloride was added (large excess of 2M solution in diethyl ether) and the mixture was stirred until it became a clear solution. Then all the volatiles were evaporated in vacuo, to give 447 mg of the title compound as white solid. ¹H NMR (300 MHz, DMSO D6) δ: 2.49-2.53 (m, 1H), 2.80-2.93 (m, 2H), 3.12-3.33 (m, 4H), 3.41 (s, 3H), 3.85-3.92 (m, 1H), 4.07-4.20 (m, 21), 6.70-6.75 (m, 2H), 6.92-7.10 (m, 5H), 7.20-7.27 (m, 1H), 9.08 (bs, 2H). LCMS (12 minutes method) [M+H]⁺=332. Rt 4.11 min.

EXAMPLE 5

Preparation of (S,R) 1-Morpholin-2-yl-1-phenyl-2-(2-trifluoromethoxy-phenyl)-ethanol hydrochloride a) 1-(4-Benzyl-morpholin-2-yl)-1-phenyl-2-(2-trifluoromethoxy-phenyl)-ethanol

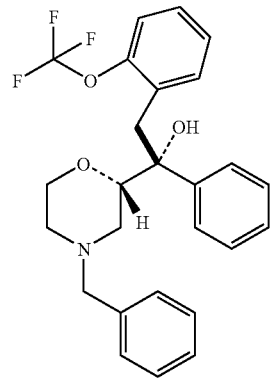

The procedure for the synthesis of example 1a, 1-(4-Benzyl-morpholin-2-yl)-2-(2-methoxy-phenyl)-1-phenyl-ethanol, was followed using 2-(trifluoromethoxy)benzyl bromide (available from Fluorochem) as starting material and making non-critical variations, to yield the title compound. FIA [M+H]⁺=458.

Alternatively, the following method may be used. Magnesium turnings (24.2 g, 0.935 mole, 2 eq.) and diethyl ether (300 ml) were loaded in a reactor under N₂. A solution of 2-trifluoromethoxybenzyl bromide (165 g, 0.647 mole, 1.3 eq.) in diethyl ether (300 ml) was loaded in an addition funnel. Iodine crystals and a small amount of the 2-trifluoromethoxybenzyl bromide solution were added and the reaction mixture was stirred to initiate the reaction. The remainder of the 2-trifluoromethoxybenzyl bromide solution was then added drop-wise maintaining the temperature of the reaction mixture below 35° C. The mixture was stirred for another 5 minutes at 23° C. after completion of the addition. A solution of (4-Benzyl-morpholin-2-yl)-phenyl-methanone (140 g, 0.498 mole) in diethyl ether (2.1 L) was added drop-wise, maintaining the temperature of the reaction mixture below 25° C. The solution obtained was stirred for 1 hour at 20° C. The reaction mixture was quenched through the addition of a saturated aqueous $NaHCO_3$ solution (700 ml) and water (700 ml). The solids were filtered and washed with diethyl ether (200 ml). The filtrates were loaded into a separation funnel and the layers were separated. The aqueous layer was extracted with diethyl ether (1 L). The organic layers were combined and the filtrates were concentrated under vacuum to about 2 liters. The solution was dried over $MgSO_4$, filtered and the filter cake was washed with diethyl ether (200 ml). The filtrate was concentrated under vacuum to orange oil. The residue was twice dissolved in toluene (500 ml) and concentrated to a solid product. The yield of crude title compound was 235 g (103%). $^1$H-NMR ($CDCl_3$): 6.80-7.07 ppm, 11H, mp; 7.04-7.01 ppm, 1H, mp; 7.01-6.86 ppm, 1H, dt; 6.84-6.80 ppm, 1H, d; 3.98-4.03 ppm, 1H, dt; 3.86-3.89 ppm, 1H, dd; 3.70-3.60 ppm, 1H, dt; 3.52-3.58 ppm, 1H, d; 3.37-3.42 ppm, 1H, d; 3.13-3.37 ppm, 1H, d; 3.05-3.08 ppm, 1H, d; 2.44-2.45 ppm, 1H, d; 2.30-2.00 ppm, 3H, mp.

b) (S,R) 1-Morpholin-2-yl-1-phenyl-2-(2-trifluoromethoxy-phenyl)-ethanol hydrochloride

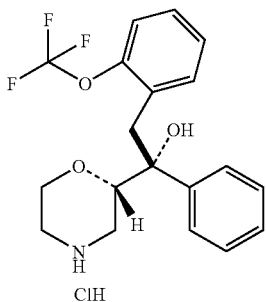

To a solution of 1-(4-Benzyl-morpholin-2-yl)-1-phenyl-2-(2-trifluoromethoxy-phenyl)-ethanol (7 g, 1 equiv.) in dry 1,2-dichloroethane (40 mL) at 0° C. under nitrogen atmosphere was added ACE-Cl (20.33 g, 10 equiv.). The reaction mixture was left to warm to room temperature for 48 hours. All volatiles were evaporated under vacuum, and the resulting solid was taken-up with methanol (50 mL) and stirred at room temperature overnight. The solution was filtered through acid ion exchange column and the required fractions evaporated to dryness. The resulting solid was taken up with acetonitrile and the insoluble material filtered off. The mother liquor was concentrated in vacuo and purified via preparative HPLC. Both fractions were mixed (from slurry and from HPLC) and taken up in ethanol. Hydrogen chloride was added (large excess of 2M solution in diethyl ether) and the mixture stirred. Then all the volatiles were evaporated in vacuo, to give 1.9 g of the title compound as a white solid (33%). $^1$H NMR (300 MHz, DMSO D6) δ: 2.45-2.50 (m, 1H), 2.81-2.97 (m, 2H), 3.18-3.30 (m, 3H), 3.89-3.97 (m, 1H), 4.15-4.18 (m, 2H), 7.02-7.29 (m, 9H), 9.18 (bs, 2H). LCMS (12 minutes method) $[M+H]^+$=368 @ Rt 4.88 min. single major peak. NET Ki=12.39 nM.

Alternatively, the following method may be used. A stainless steel Buchi hydrogenation reactor was loaded with 1-(4-Benzyl-morpholin-2-yl)-1-phenyl-2-(2-trifluoromethoxy-phenyl)-ethanol (230 g, 0.503 mole), methanol (1 L), a suspension of Pd/C (10%, 46 g, 20% loading) in methanol (500 ml), and methanol (500 ml) from equipment rinses. A solution of HCl in ethanol (1.6N, 460 ml, 0.736 mole, 1.5 eq.) was added and the reactor was pressurized with $H_2$ (3 Bar). The reaction mixture was heated to 40° C. and stirred for 3 hours. The reaction mixture was cooled to 20° C. and flushed with $N_2$. The catalyst was filtered off and washed with methanol (0.5 L). The filtrates were concentrated under vacuum to a yellow solid. The yield of crude title compound was 198 g (97.5%). A reactor was loaded with crude title compound (190 g, 0.47 mole) and toluene (6.65 L) under $N_2$. The suspension was heated under reflux and toluene (150 ml) was added until all solid dissolved. The solution was stirred for 15 minutes more under reflux and then cooled slowly to 20° C. The suspension was stirred for 1 hour at 20° C. The solid was filtered, washed with toluene (680 ml), and dried at 40° C. under vacuum. The yield of pure anhydrous title compound was 158.5 g (83.4%).

Alternatively, the following method may be used. In a glass-lined nitrogen purged hydrogenator are charged 1-(4-Benzyl-morpholin-2-yl)-1-phenyl-2-(2-trifluoromethoxy-phenyl)-ethanol hydrochloride (150 g, 303.7 mmol), demineralized water (352 mL), i-PrOH (375 mL) and 5% Pd/C (30 g, 50% water, Johnson & Matthey type 440). The heterogeneous reaction mixture was then purged 5 times with 25 psi nitrogen then purged 5 times with 50 psi hydrogen, and the hydrogenation was performed at RT. The initial Tmass was 22° C. and the maximum Tmass during the hydrogenation was 23° C. The reactor was stirred vigorously. In-process analysis after 2 hours indicated complete hydrogenolysis. The hydrogenation was stopped after 3 hours. The nitrogen purged reaction mixture was then filtered at RT through an hyflo filter (56 g), impregnated beforehand with 75 mL of a 50/50 v/v isopropanol/water mixture and washed with 300 mL of a 50/50 v/v isopropanol/water mixture. The filtrates were stored overnight at RT. The filtrates were concentrated at 40-50° C. under reduced pressure (typical 622 g distilled). The reaction mixture was cooled to RT and post-agitated. After 3 hours, 1 mL of the solution was taken and cooled to 0° C. to initiate crystallization. These seeds were added to the reaction mixture and precipitation was observed within a few minutes. The mixture was post-agitated at RT for 2 hours. The crystals were filtered and rinsed with $H_{2O}$ (30 mL). Then, the precipitate was dried under reduced pressure (400 mmHg) with a nitrogen flow (0.1 bar) for 4 hours affording the title compound as the hydrate polymorph (103.5 g, 81% yield).

EXAMPLE 6

Preparation of (S,R) 2-Biphenyl-2-yl-1-morpholin-2-yl-1-phenyl-ethanol hydrochloride a) 1-(4-Benzyl-morpholin-2-yl)-2-biphenyl-2-yl-1-phenyl-ethanol

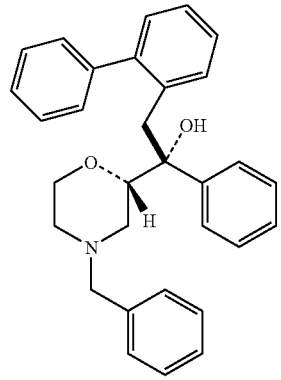

1-(4-Benzyl-morpholin-2-yl)-2-(2-bromo-phenyl)-1-phenyl-ethanol (0.50 g, 1.0 equiv. prepared according to Example 15a below) and phenylboronic acid (0.402 g, 3.0 equiv., available from Aldrich Chemical Company) were suspended in a mixture ethanol/water (2/1, 7.5 mL) and Pd(Ph$_3$)$_4$ (0.022 g, 0.04 equiv.), then K$_2$CO$_3$ (0.654 g, 4.30 equiv.) were added. The mixture was heated to 80° C. under nitrogen atmosphere. After 16 hours, the reaction was cooled down to room temperature and filtered through Celite, then extracted with ethyl acetate. The organic layers were combined, dried with MgSO$_4$, filtered and concentrated in vacuo yielding a yellow oil, which was purified by column chromatography on silica gel (10% EtOAc:Hexane) to give 0.491 g (98%) of the title compound as a white solid.

b) (S,R) 2-Biphenyl-2-yl-1-morpholin-2-yl-1-phenyl-ethanol hydrochloride

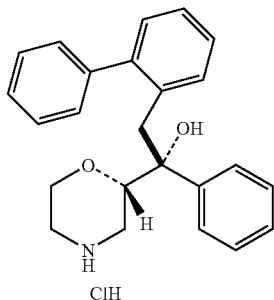

The procedure for the synthesis of example 1b, 2-(2-methoxy-phenyl)-1-morpholin-2-yl-1-phenyl-ethanol hydrochloride, was followed making non-critical variations, to yield the title compound. $^1$H NMR (300 MHz, DMSO D6) δ: 2.16-2.20 (m, 1H), 2.54-2.62 (m, 1H), 2.67-2.76 (m, 1H), 2.85-2.89 (m, 1H), 3.24 (s, 2H), 3.61-3.69 (m, 2H), 3.93-3.98 (m, 1H), 5.14 (bs, 1H), 6.80-6.92 (m, 5H), 7.04-7.17 (m, 5H), 7.27-7.30 (m, 3H), 7.36-7.39 (m, 1H). LCMS (12 minutes method) [M+H]$^+$=360 @ Rt 5.15 min. single major peak.

EXAMPLE 7

Preparation of (S,R) 2-(2-Chloro-phenyl)-1-morpholin-2-yl-1-phenyl-ethanol hydrochloride a) 1-(4-Benzyl-morpholin-2-yl)-2-(2-chloro-phenyl)-1-phenyl-ethanol

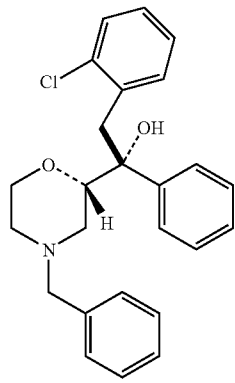

The procedure for the synthesis of example 1a, 1-(4-Benzyl-morpholin-2-yl)-2-(2-methoxy-phenyl)-1-phenyl-ethanol, was followed using 2-chlorobenzyl chloride (available from Aldrich Chemical Company) as starting material and making non-critical variations, to yield the title compound. FIA [M+H]$^+$=408 and 410.

b) (S,R) 2-(2-Chloro-phenyl)-1-morpholin-2-yl-1-phenyl-ethanol hydrochloride

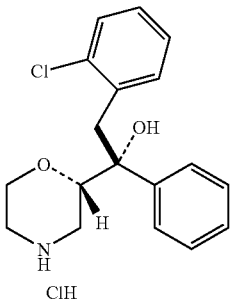

The procedure for the synthesis of example 5b, (S,R) 1-Morpholin-2-yl-1-phenyl-2-(2-trifluoromethoxy-phenyl)-ethanol hydrochloride, was followed making non-critical variations, to yield the title compound. $^1$H NMR (300 MHz, DMSO D6) δ: 2.45-2.54 (m, 1H), 2.84-2.93 (m, 2H), 3.17-3.22 (m, 1H), 3.33-3.38 (m, 3H), 3.89-3.97 (m, 1H), 4.14-4.18 (m, 2H), 7.06-7.11 (m, 2H), 7.15-7.26 (m, 7H), 9.24 (bs, 2H) ppm. LCMS (12 minutes method) [M+]$^+$=318-320 @ Rt 4.36 min. single peak.

EXAMPLE 8

Preparation of (S,R) 2-(5-Fluoro-2-methoxy-phenyl)-1-morpholin-2-yl-1-phenyl-ethanol hydrochloride a) 1-(4-Benzyl-morpholin-2-yl)-2-(5-fluoro-2-methoxy-phenyl)-1-phenyl-ethanol

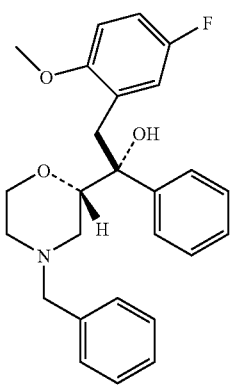

The procedure for the synthesis of example 1a, 1-(4-Benzyl-morpholin-2-yl)-2-(2-methoxy-phenyl)-1-phenyl-ethanol, was followed using 2-chloromethyl-4-fluoro-1- methoxy-benzene (synthesized as described above) as starting material making non-critical variations, to yield the title compound which was taken without further purification in the next step. LCMS (6 minutes method) [M+H]⁺=422 @ Rt 2.85 min. major peak.

Alternatively, the following method may be used. Magnesium turnings (21.6 g, 0.888 mole, 2 eq.) and diethyl ether (300 ml) were loaded in a reactor under $N_2$. A solution of 5-fluoro-2-methoxybenzyl chloride (116 g, 0.664 mole, 1.5 eq.) in diethyl ether (200 ml) was loaded in an addition funnel. Iodine crystals and a small amount of the 5-fluoro-2-methoxybenzyl chloride solution were added and the reaction mixture was stirred to initiate the reaction. The remainder of the 5-fluoro-2 methoxybenzyl chloride solution was then added drop-wise maintaining the temperature of the reaction mixture below 28° C. The mixture was stirred for another 5 minutes at 19° C. after completion of the addition and a white suspension was formed. A solution of (4-Benzyl-morpholin-2-yl)-phenyl-methanone (125 g, 0.444 mole) in diethyl ether (1.8 L) was added drop-wise, maintaining the temperature of the reaction mixture below 25° C. The suspension obtained was stirred for 2 hours. The reaction mixture was quenched through the addition of a saturated aqueous $NaHCO_3$ solution (625 ml) and water (500 ml), maintaining the temperature below 20° C. The mixture was stirred for 30 minutes and the solids were filtered, washed with water (125 ml) and diethyl ether (200 ml). The filtrates were loaded into a separation funnel and the layers were separated. The aqueous layer was extracted with diethyl ether (1 L). The organic layers were combined and dried over $MgSO_4$, filtered and the filter cake was washed with diethyl ether (100 ml). The filtrates were concentrated under vacuum. The yield of title compound was 201 g as a yellow solid (107%). Title compound (200 g, 0.474 mole) was then suspended in isopropanol (400 ml) under $N_2$. The suspension was heated under reflux until all solids were dissolved. The solution is allowed to cool to 20° C. over 4 hours under stirring. The solid is filtered, washed with isopropanol (100 ml) and dried at 40° C. under vacuum. The yield of pure title compound is 158 g (79%). ¹H-NMR (CDCl₃): 6.99-7.26 ppm, 10H, mp; 6.60-6.71 ppm, 1H, dt; 6.49-6.60 ppm, 1H, dd; 6.31-6.44 ppm, 1H, dd; 3.92-4.01 ppm, 1H, dt; 3.80-3.90 ppm, 1H, dd; 3.64-3.73 ppm, 1H, dd; 3.59-3.64 ppm, 1H, d; 3.52-3.59 ppm, 3+1 H, 2s; 3.37-3.45 ppm, 1H, d; 3.07-3.17 ppm, 1H, d; 2.84-2.92 ppm, 1H, d; 2.43-2.53 ppm, 1H, d; 2.20-2.28 ppm, 1H, d; 1.98-2.11 ppm, 2H, mp.

b) (S, R) 2-(5-Fluoro-2-methoxy-phenyl)-1-morpholin-2-yl-1-phenyl-ethanol hydrochloride

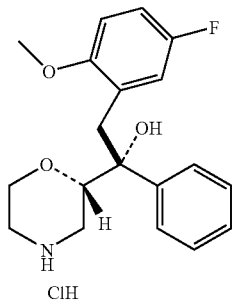

The procedure for the synthesis of 1b, 2-(2-Methoxy-phenyl)-1-morpholin-2-yl-1-phenyl-ethanol hydrochloride was followed making non-critical variations, to yield the title compound. ¹H NMR (300 MHz, DMSO D6) δ: 2.44- 2.50 (m, 1H), 2.79-2.96 (m, 2H), 3.15-3.20 (m, 2H), 3.27-3.33 (m, 2H), 3.42 (s, 3H), 3.86-3.94 (m, 1H), 4.09-4.18 (m, 2H), 6.66-6.71 (m, 1H), 6.80-6.90 (m, 2H), 7.14-7.23 (m, 5H), 9.20 (bs, 2H). LCMS (12 minutes method) [M+H]⁺=332. NET Ki=3.60 nM.

Alternatively, the following method may be used. A glass hydrogenation flask was loaded with methanol (1.55 L), Pd/C (10%, 31 g, 20% loading), 1-(4-benzyl-morpholin-2-yl)-2-(5-fluoro-2-methoxy-phenyl)-1-phenyl-ethanol (155 g, 0.368 mole) and a solution of HCl in ethanol (2.5N, 233 ml, 0.582 mole, 1.6 eq.). The reactor was mounted on a Parr instrument and pressurized with $H_2$ (49 Psi). The reaction mixture was shaken overnight between 20° C. and 15° C. The catalyst was filtered off and washed with methanol (0.5 L). The filtrates were concentrated under vacuum. The yield of crude title compound was 109.5 g (81%). The catalyst was washed again with methanol (2×500 ml). The filtrates were combined and concentrated under vacuum. The yield of the second crop of crude title compound was 21.7 g (16%). A reactor was loaded with crude title compound (131 g, 0.356 mole) and isopropanol (1.3 L) under $N_2$. The suspension was heated under reflux for 4 hours. The mixture was cooled to 20° C. and the solid was filtered, washed with isopropanol (130 ml), and dried at 50° C. under vacuum. The yield of pure title compound was 115.9 g (88.5% yield).

EXAMPLE 9

Preparation of (S,R) 1-Morpholin-2-yl-1-phenyl-2-(2-trifluoromethylsulfanyl-phenyl)-ethanol acetate a) 1-(4-Benzyl-morpholin-2-yl)-1-phenyl-2-(2-trifluoromethylsulfanyl-phenyl)-ethanol

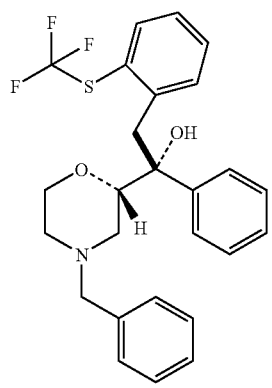

The procedure for the synthesis of example 1a, 1-(4-benzyl-morpholin-2-yl)-2-(2-methoxy-phenyl)-1-phenyl-ethanol, was followed using 1-bromomethyl-2-trifluoromethylsulfanyl-benzene (available from Fluorochem Ltd.) as starting material and making non-critical variations, to yield the title compound. ¹H NMR (300 MHz, CDCl₃) δ: 2.05-2.33 (m, 3H), 2.49-2.65 (m, 1H), 3.10-3.35 (m, 2H), 3.43-3.55 (m, 1H), 3.67-3.89 (m, 2H), 3.91-4.08 (m, 2H), 4.09-4.22 (m, 1H), 6.91-7.05 (m, 1H), 7.10-7.42 (m, 12H), 7.50-7.63 (m, 1H) ppm.

b) (S,R) 1-Morpholin-2-yl-1-phenyl-2-(2-trifluoromethylsulfanyl-phenyl)-ethanol acetate

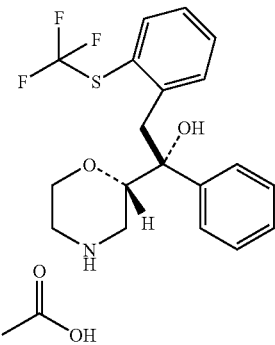

To a solution of 1-(4-benzyl-morpholin-2-yl)-1-phenyl-2-(2-trifluoromethylsulfanyl-phenyl)-ethanol (218 mg g, 1 equiv.) and solid supported Hunig's base (available from Argonaut, 1 g, 5 equiv.) in dry tetrahydrofuran (4 mL) at 0° C. under nitrogen atmosphere was added ACE-Cl (502 µL, 10 equiv.). The reaction mixture was left to warm to room temperature for 48 hours. All volatiles were evaporated under vacuum, and the resulting solid was taken-up with methanol (50 mL) and stirred at room temperature overnight. The solution was filtered through acid ion exchange column and the required fractions evaporated to dryness. The resulting solid was purified via preparative HPLC to give 62 mg of the title compound as a colourless oil. $^1$H NMR (300 MHz, CDCl$_3$) δ: 2.01 (s, 3H), 2.43-2.47 (m, 1H), 2.63-2.70 (m, 1H), 2.81-2.94 (m, 2H), 3.24 (d, 1H, J=13.57 Hz), 3.85-3.96 (m, 2H), 4.01-4.05 (m, 1H), 4.09-4.13 (m, 1H), 4.45 (bs, 4H), 6.90-6.93 (m, 1H), 7.13-7.26 (m, 7H), 7.55-7.58 (m, 1H) ppm. LCMS (12 minute method) $[M+H]^+$ =384 @ Rt 5.13 min. single peak.

EXAMPLE 10

Preparation of (S,R) 1-Morpholin-2-yl-1-phenyl-2-(2-trifluoromethyl-phenyl)-ethanol a) 4-Benzyl-2-(2-phenyl-oxiranyl)-morpholine

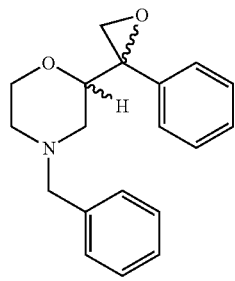

To a mixture of trimethylsulfoxonium iodide (783 mg, 1 equiv.) and sodium hydride (142 mg, 1 equiv.) in dimethylformamide (17 mL) at 0° C. under nitrogen atmosphere was added dimethylsulfoxide (251 µL, 1 equiv.) and the resulting suspension was stirred for 30 minutes. A solution of (4-Benzyl-morpholin-2-yl)-phenyl-methanone (1 g, 1 equiv.) in dimethylformamide (10 mL) was then added dropwise. Stirring was continued for 30 minutes and the reaction was stopped by addition of water (50 mL). The aqueous solution was extracted with diethyl ether, the organic phase dried with MgSO$_4$, and evaporated in vacuo. The crude material was purified using a column chromatography on silica gel eluting with a mixture of ethyl acetate/heptane (20/80) to give 825 mg of the title compound as a colourless oil (78%), mixture of two diastereoisomers. LCMS (6 minute method) $[M+H]^+$=296 @ Rt 1.88 min. single peak.

b) 1-(4-Benzyl-morpholin-2-yl)-1-phenyl-2-(2-trifluoromethyl-phenyl)-ethanol

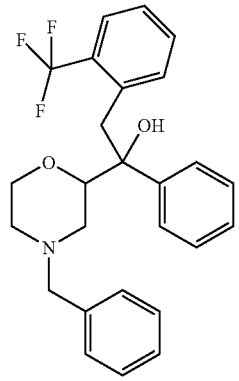

To a suspension of magnesium turnings in tetrahydrofuran (2 mL) at room temperature under nitrogen atmosphere was added a solution of 1-bromo-2-trifluoromethyl-benzene (7.6 g, 5 equiv., available from Acros) in tetrahydrofuran (32 mL) and the mixture was stirred for an hour. The solution was cooled to −78° C. and copper iodide (646 mg) was added followed by dropwise addition of a solution of 4-Benzyl-2-(2-phenyl-oxiranyl)-morpholine (2 g, 1 equiv.) in tetrahydrofuran (10 mL). The resulting mixture was warmed to room temperature over 2 hours and then treated with water (10 mL). The solution was extracted with diethyl ether, the organic phase dried with MgSO$_4$, and evaporated in vacuo. The crude material was purified using a column chromatography on silica gel eluting with a mixture of ethyl acetate/heptane (10/90) to give 352 mg of the title compound as a colourless oil (12%). LCMS (6 minutes method) $[M+H]^+$=442 @ Rt 3.05 min. major peak.

c) (S,R) 1-Morpholin-2-yl-1-phenyl-2-(2-trifluoromethyl-phenyl)-ethanol

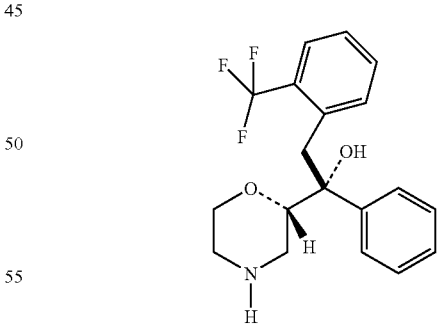

To a solution of 1-(4-Benzyl-morpholin-2-yl)-1-phenyl-2-(2-trifluoromethyl-phenyl)-ethanol (352 mg, 1 equiv.) in ethanol (15 mL) at room temperature under nitrogen atmosphere was added ammonium formate (507 mg g, 10 equiv.) followed by addition of palladium on charcoal (10%, 355 mg.). The reaction mixture was heated to reflux for 1 hour, cooled to room temperature and then filtered through Celite. All volatiles were evaporated under vacuum to give 265 mg of the title compound as white solid (94%). The enantiomeric mixture was resolved using chiral HPLC, to give the title compound as a single enantiomer. ¹H NMR (300 MHz, CDCl₃) δ: 2.25-2.30 (m, 1H), 2.56-2.64 (m, 1H), 2.75-2.87 (m, 2H), 3.18 (d, 1H, J=14.88 Hz), 3.71-3.81 (m, 2H), 3.89 (d, 1H, J=14.88 Hz), 4.02-4.05 (m, 1H), 6.83-6.86 (m, 1H), 7.09-7.34 (m, 7H), 7.53-7.55 (m, 1H) ppm. LCMS (12 minute method) [M+H]⁺=352 @ Rt 4.73 min. single peak.

EXAMPLE 11

Preparation of (S,R) 2-(2-Chloro-phenyl)-1-(3-fluoro-phenyl)-1-morpholin-2-yl-ethanol hydrochloride a) 1-(4-Benzyl-morpholin-2-yl)-2-(2-chloro-phenyl)-1-(3-fluoro-phenyl)-ethanol

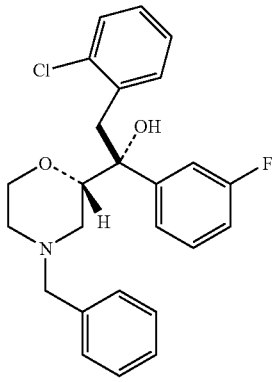

The procedure for the synthesis of 4a, 1-(4-Benzyl-morpholin-2-yl)-1-(3-fluoro-phenyl)-2-(2-methoxy-phenyl)-ethanol was followed using 2-chorobenzyl chloride (available from Aldrich Chemical Company) as starting material, and making non-critical variations, to yield the title compound which was taken without further purification in the next step. LCMS (6 minutes method) [M+H]⁺=426 @ Rt 2.85 min. major peak.

b) (S,R) 2-(2-Chloro-phenyl)-1-(3-fluoro-phenyl)-1-morpholin-2-yl-ethanol hydrochloride

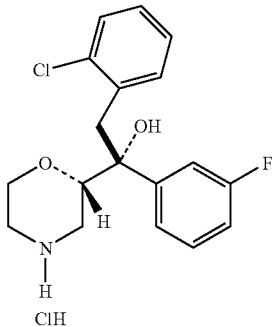

To a solution of 1-(4-Benzyl-morpholine-2-yl)-2-(2-chloro-phenyl)-1-(3-fluoro-phenyl)-ethanol. (3.2 g, 1 equiv.) in dry 1,2-dichloroethane (40 mL) under nitrogen atmosphere was added ACE-Cl (20.33 g, 5 equiv.). The reaction mixture was stirred at room temperature overnight then refluxed until completion. All volatiles were evaporated under vacuum, and the resulting residue redissolved in acetonitrile. This solution was filtered through an ion exchange column and the filtrate taken-up with methanol (50 mL) and refluxed for 3 h. The solution was again filtered through acid ion exchange column and the required fractions evaporated to dryness. The resulting solid was next purified via preparative HPLC followed by chiral HPLC. The purified active enantiomer was taken up in ethanol and hydrogen chloride was added (large excess of 2M solution in diethyl ether) and the mixture stirred. Then all the volatiles were evaporated in vacuo, to give 519 mg of the title compound as a white solid (18%). ¹H NMR (300 MHz, DMSO D6) δ: 2.43-2.54 (m, 1H), 2.81-2.95 (m, 2H), 3.16-3.23 (m, 1H), 3.30-3.44 (m, 2H), 3.54 (bs, 1H), 3.92-4.00 (m, 1H), 4.15-4.23 (m, 2H), 6.96-7.29 (m, 8H), 9.32-9.45 (m, 2H). LCMS (12 minute method) [M+H]⁺=336.

EXAMPLE 12

Preparation of (S,R) 1-Morpholin-2-yl-1-phenyl-2-o-tolyl-ethanol hydrochloride a) 1-(4-Benzyl-morpholin-2-yl)-1-phenyl-2-o-tolyl-ethanol

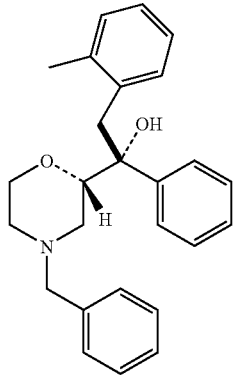

The procedure for the synthesis of example 1a, 1-(4-benzyl-morpholin-2-yl)-2-(2-methoxy-phenyl)-1-phenyl-ethanol, was followed using commercially available 2-methylbenzylmagnesium bromide (available from Rieke-Metals) as starting material and making non-critical variations, to yield the title compound. FIA [M+H]⁺=388.

b) (S,R) 1-Morpholin-2-yl-1-phenyl-2-o-tolyl-ethanol hydrochloride

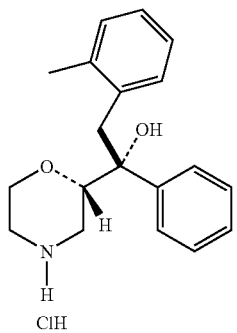

The procedure for the synthesis of example 1b, 2-(2-methoxy-phenyl)-1-morpholin-2-yl-1-phenyl-ethanol hydrochloride was followed making non-critical variations, to yield the title compound $^1$H NMR (300 MHz, DMSO D6) δ: 1.62 (s, 3H), 2.40-2.58 (m, 1H), 2.78-3.01 (m, 2H), 3.03-3.09 (m, 1H), 3.15-3.31 (m, 2H), 3.90-4.05 (m, 1H), 4.15-4.25 (m, 2H), 6.89-7.28 (m, 9H), 9.21-9.55 (m, 2H). LCMS (12 minute method) [M+]$^+$=298 single peak.

EXAMPLE 13

Preparation of (S,R) 1-Morpholin-2-yl-1,2-diphenyl-ethanol hydrochloride a) 1-(4-Benzyl-morpholin-2-yl)-1,2-diphenyl-ethanol

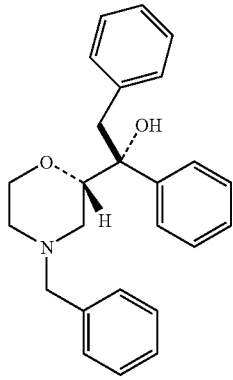

The procedure for the synthesis of example 1a, 1-(4-benzyl-morpholin-2-yl)-2-(2-methoxy-phenyl)-1-phenyl-ethanol, was followed using commercially available benzylmagnesium bromide (available from TCI America) as starting material and making non-critical variations, to yield the title compound. LCMS [M+H]$^+$=374.1 major single peak @ 3.82 min.

b) (S,R) 1-Morpholin-2-yl-1,2-diphenyl-ethanol hydrochloride

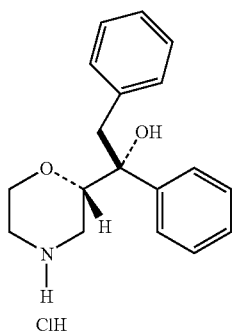

The procedure for the synthesis of example 1b, 2-(2-methoxy-phenyl)-1-morpholin-2-yl-1-phenyl-ethanol hydrochloride was followed making non-critical variations, to yield the title compound. $^1$H NMR (300 MHz, CDCl$_3$) δ: 2.36-2.41 (m, 1H), 2.64-2.71 (m, 1H), 2.78-2.91 (m, 3H), 3.16-3.32 (m, 2H), 3.73-3.82 (m, 2H), 4.08-4.11 (m, 1H), 6.80-6.83 (m, 2H), 7.07-7.12 (m, 3H), 7.16-7.27 (m, 6H). LCMS [M+H]$^+$=284.1 single peak @ 3.82 minutes.

EXAMPLE 14

Preparation of (S,R) 2-(2-Fluoro-phenyl-1-morpholin-2-yl-1-phenyl-ethanol hydrochloride a) 1-(4-Benzyl-morpholin-2-yl)-2-(2-fluoro-phenyl)-1-phenyl-ethanol

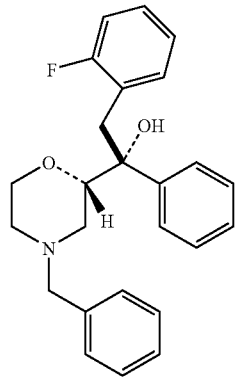

The procedure for the synthesis of example 1a, 1-(4-benzyl-morpholin-2-yl)-2-(2-methoxy-phenyl)-1-phenyl-ethanol, was followed using commercially available 2-fluoro-benzylmagnesium chloride (available from Rieke Metals) as starting material and making non-critical variations, to yield the title compound. FIA [M+H]$^+$=392.1.

b) (S,R) 2-(2-Fluoro-phenyl)-1-morpholin-2-yl-1-phenyl-ethanol hydrochloride

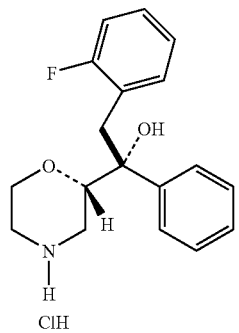

The procedure for the synthesis of example 1b, 2-(2-methoxy-phenyl)-1 morpholin-2-yl-1-phenyl-ethanol hydrochloride was followed making non-critical variations, to yield the title compound. $^1$H NMR (300 MHz, DMSO D6) δ: 2.40-2.56 (m, 1H), 2.78-2.97 (m, 2H), 3.17-3.29 (m, 3), 3.89-3.96 (m, 1H), 4.14-4.19 (m, 2H), 5.47 (bs, 1H), 6.82-6.94 (m, 2H), 7.01-7.25 (m, 7H), 9.28-9.38 (m, 2H). LCMS [M+H]$^+$=302.1 single major peak @ 3.82 minutes.

EXAMPLE 15

Preparation of (S,R) 2-(2-bromo-phenyl)-1-phenyl-1-morpholin-2-yl-ethanol a) 1-(4-Benzyl-morpholin-2-yl)-2-(2-bromo-phenyl)-1-phenyl-ethanol

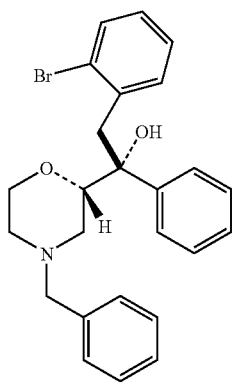

The procedure for the synthesis of example 1a, 1-(4-Benzyl-morpholin-2-yl)-2-(2-methoxy-phenyl)-1-phenyl-ethanol, was followed using commercially available 2-bromobenzylmagnesium bromide (available from Rieke-Metals) as starting material and making non-critical variations, to yield the title compound. FIA [M+H]$^+$=452/454.

b) (S,R) 1-Morpholin-2-yl-2-(2-bromo-phenyl)-1-phenyl-ethanol

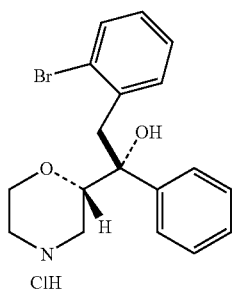

The procedure for the synthesis of example 5b, (S, R) 1-Morpholin-2-yl-1-phenyl-2-(2-trifluoromethoxy-phenyl)-ethanol, was followed making non-critical variations, to yield the title compound. $^1$H NMR (300 MHz, CDCl$_3$) δ: 2.64-2.68 (m, 1H), 3.02-3.21 (m, 2H), 3.27-3.33 (m, 3H), 3.45-3.50 (m, 1H), 3.63-3.68 (m, 1H), 3.99-4.09 (m, 1H), 4.20-4.24 (m, 1H), 4.29-4.34 (m, 1H), 4.87 (s, 1H), 6.98-7.21 (m, 2H), 7.24-7.59 (m, 7H) ppm. LCMS (6 minutes method) [M+H]$^+$=362.3 @ Rt 2.85 min. single peak.

EXAMPLE 16

Preparation of (S,R) 2-(2'-chloro[1-1'biphenyl]-2-yl)-1-morpholin-2-yl-1-phenyl-ethanol hydrochloride a) 2-(2'-chloro[1-1'biphenyl]-2-yl)-1-phenyl-1-[4-(phenylmethyl)morpholin-2-yl]ethanol

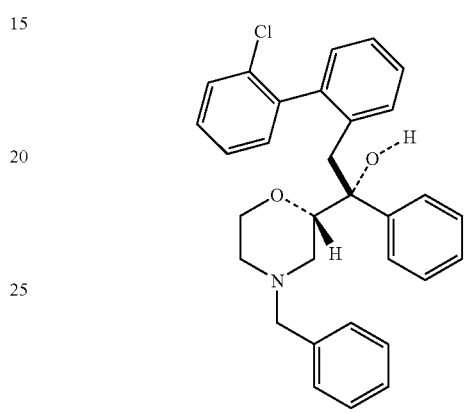

The procedure for the synthesis of example 6a, was followed using 2-chloro phenyl boronic acid (available from Aldrich Chemical Company) as starting material and making non-critical variations, to yield the title compound. FIA [M+H]$^+$=485 b) (S, R) 2-(2'-chloro[1-1'biphenyl]-2-yl)-1-morpholin-2-yl-1-phenyl-ethanol hydrochloride

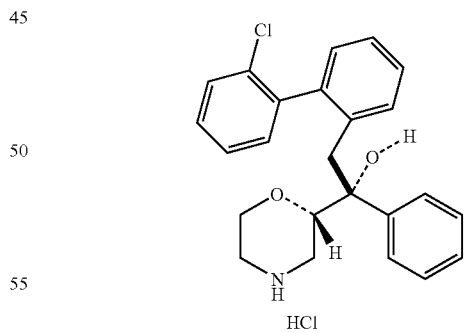

The procedure for the synthesis of example 6b, was followed making non-critical variations, to yield the title compound. $^1$H NMR (300 MHz, CDCl$_3$) δ: 2.10-2.21 (m, 1H), 2.57-2.65 (m, 1H), 2.62-2.75 (m, 1H), 2.83-2.87 (m, 1H), 3.20 (s, 2H), 3.63-3.70 (m, 2H), 3.95-3.97 (m, 1H), 5.12 (bs, 1H), 6.80-6.92 (m, 5H), 7.04-7.17 (m, 5H), 7.27-7.37 (m, 3H). LCMS (12 minutes method) [M+H]$^+$=393 @ Rt 4.75 min. single major peak.

EXAMPLE 17

Preparation of 4-Fluoro-2-(2-morpholin-2-yl-2-phenylpropyl)phenol hydrochloride a) 4-Fluoro-2-(2-morpholin-2-yl-2-phenylpropyl)phenol hydrochloride

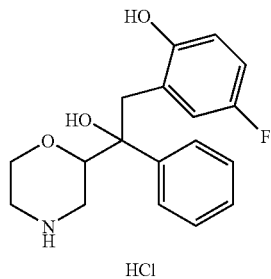

HCl

Sodium thiomethoxide (13 eq, 186 mg) was added at once to a solution of 2-{2-[5-fluoro-2-(methyloxy)phenyl]-1-methyl-1-phenylethyl}morpholine hydrochloride (75.2 mg, 0.204 mmol, synthesized as described in Example 8 above) in anydrous DMF (3 ml) in a microwave vessel. Upon addition, the reaction vessel was sealed and heated up in a CEM-Discovery microwave at 150 Watts, reaching 110° C. in 5 minutes and maintaining this temperature 6 minutes. The reaction vessel was cooled to room temperature and the reaction mixture taken into methanol (5 ml) and purified by SCX-2 chromatography to obtain the free base as clear oil (50 mg). The hydrochloride salt was obtained following general procedures as a white solid (52 mg, 72% after salt formation.). MW 353.83; $C_{18}H_{22}NO_3FCl$; $^1H$ NMR ($CD_3OD$): 7.29-7.26 (2H, m), 7.20-7.08 (2H, m), 6.53-6.50 (2H, m), 6.30-6.26 (1H, m), 4.18 (1H, dd, 12.6 Hz, 2.6 Hz), 4.02 (1H, dd, 10.9 Hz, 2.3 Hz), 3.86 (1H, td, 12.6 Hz, 2.6 Hz), 3.60 (1H, 1/2 AB), 3.16 (1H, d, 12.6 Hz), 3.08-2.90 (3H, m), 2.58 (1H, m); $^{19}F$ NMR ($CD_3OD$)-128.4; LCMS: (12 min method) m/z 318.1 $[M-HCl+H]^+$ @ Rt 3.954 min.

EXAMPLE 18

Preparation of 2-(2-Fluoro-6-chloro-phenyl)-1-morpholin-2-yl-1-phenyl-ethanol hydrochloride a) 1-(4-Benzyl-morpholin-2-yl)-2-(2-chloro-6-fluoro-phenyl)-1-phenyl-ethanol

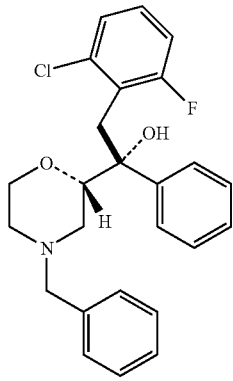

To a stirred solution of 2-chloro-6-fluorobenzyl magnesium chloride (12.8 mL, 3.20 mmol, 3 equiv., available from Rieke Metals) in anhydrous tetrahydrofuran (15 ml) at 0° C. under nitrogen was added a solution of (4-Benzyl-morpholin-2-yl)-phenyl-methanone (300 mg, 1.07 mmol, 1 equiv.) in tetrahydrofuran (5 ml) dropwise over 15 minutes. The reaction was then stirred at 0° C. for one hour. The reaction mixture was allowed to warn to room temperature over two hours and stirred for a further 18 h. The solvent was then evaporated "in vacuo" and the residue redissolved in dichloromethane (30 mL). The organic solution was washed with aqueous saturated solution of $NaHCO_3$ (50 mL). The aqueous solution was extracted with dichloromethane using a hydrophobic phase separator. The dichloromethane was evaporated "in vacuo" and redissolved in methanol (2 mL). The sample was bound to SCX-2 (5 g) and washed with methanol (30 mL). The sample was eluted using 2M ammonia in methanol (30 mL). The solvent was then evaporated using a reacti-therm blow down station to give 450 mg of a yellow amorphous solid. This material was used in step b) without further purification. LCMS (6 minutes method) $[M+H]^+=426$ @ Rt 3.27 min. major peak.

b) 2-(2-Fluoro-6-chloro-phenyl)-1-morpholin-2-yl-1-phenyl-ethanol hydrochloride

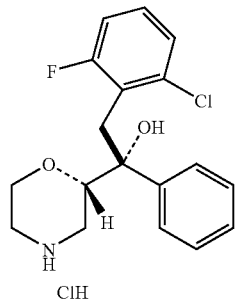

ClH

To a solution of 1-(4-Benzyl-morpholin-2-yl)-2-(2-chloro-6-fluoro-phenyl)-1-phenyl-ethanol (450 mg, 1 equiv.) in ethyl acetate (15 mL) at room temperature under nitrogen atmosphere was added ammonium formate (1.69 g, 25 equiv.) followed by addition of palladium on charcoal (10%, 450 g.). The reaction mixture was heated to reflux for 1.5 hours, cooled to room temperature and then filtered through Celite. All volatiles were evaporated under vacuum, and the resulting solid was purified via preparative HPLC. The isolated white solid was taken up in ethanol. Hydrogen chloride was added (large excess of 2M solution in diethyl ether) and the mixture was stirred until it became a clear solution. Then all the volatiles were evaporated "in vacuo", to give 147 mg of the title compound as white solid. $^1H$ NMR (300 MHz, $CD_3OD$ D4) δ: 2.51-2.61 (d, 1H), 2.79-2.91 (t, 1H), 2.96-3.09 (m, 1H), 3.09-3.16 (m, 1H), 3.32-3.54 (q, 2H), 3.82-3.97 (t, 1H), 4.09-4.24 (t, 2H), 6.73-6.84 (t, 1H), 6.93-7.08 (m, 2H), 7.08-7.21 (m, 5H). LCMS (12 minutes method) $[M+H]^+=336$ @ Rt 4.44 min. single major peak.

EXAMPLE 19

Preparation of 2-(2,5-Dimethoxy-phenyl)-1-morpholin-2-yl-1-phenyl-ethanol hydrochloride a) 1-(4-Benzyl-morpholin-2-yl)-2-(2,5-dimethoxy-phenyl)-1-phenyl-ethanol

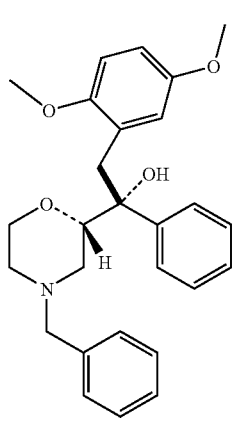

The procedure for the synthesis of example 18a, 1-(4-Benzyl-morpholin-2-yl)-2-(2-chloro-6-fluoro-phenyl)-1-phenyl-ethanol, using 2,5-dimethoxybenzyl magnesium chloride as starting material (available from Rieke Metals) was followed making non-critical variations, to yield the title compound. This material was used in step b) without further purification. LCMS (6 minutes method) [M+H]$^+$=434 @ Rt 3.10 min. major peak.

b) 2-(2,5-Dimethoxy-phenyl)-1-morpholin-2-yl-1-phenyl-ethanol hydrochloride

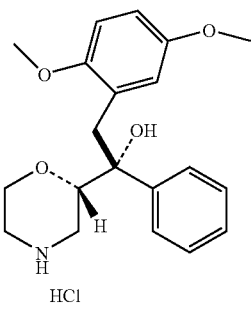

The procedure for the synthesis of example 18b, 2-(2-Fluoro-6-chloro-phenyl)-1-morpholin-2-yl-1-phenyl-ethanol hydrochloride, was followed making non-critical variations, to yield the title compound. $^1$H NMR (300 MHz, CD$_3$OD D4) δ: 2.53-2.62 (d, 1H), 2.86-3.10 (m, 3H), 3.13-3.27 (m, 2H), 3.36-3.51 (m, 6H), 3.81-3.93 (t, 1H), 4.02-4.08 (d, 1H), 4.15-4.25 (d, 1H), 6.28-6.33 (s, 1H), 6.49-6.64 (m, 2H), 7.06-7.22 (m, 5H). LCMS (12 minutes method) [M+H]$^+$=344 @ Rt 4.15 min. single major peak.

EXAMPLE 20

Preparation of 2-(2,4-Difluoro-phenyl)-1-morpholin-2-yl-1-phenyl-ethanol hydrochloride a) 1-(4-Benzyl-morpholin-2-yl)-2-(2,4-difluoro-phenyl)-1-phenyl-ethanol

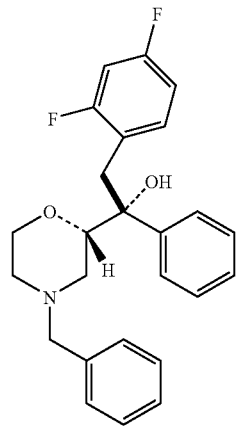

The procedure for the synthesis of example 18a, 1-(4-Benzyl-morpholin-2-yl)-2-(2-chloro-6-fluoro-phenyl)-1-phenyl-ethanol, using 2,4-difluorobenzyl magnesium bromide as starting material (available from Rieke Metals) was followed making non-critical variations, to yield the title compound. This material was used in step b) without further purification. LCMS (6 minutes method) [M+H]$^+$=410 @ Rt 3.19 min. major peak.

b) 2-(2,4-Difluoro-phenyl)-1-morpholin-2-yl-1-phenyl-ethanol hydrochloride

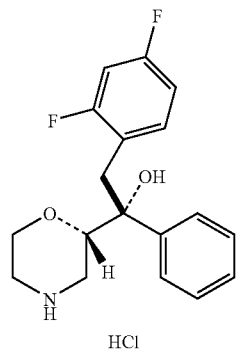

The procedure for the synthesis of example 18b, 2-(2-Fluoro-6-chloro-phenyl)-1-morpholin-2-yl-1-phenyl-ethanol hydrochloride, was followed making non-critical variations to yield the title compound. $^1$H NMR (300 MHz, CD$_3$OD D4) δ: 2.48-2.59 (d, 1H), 2.87-3.09 (m, 2H), 3.11-3.17 (m, 2H), 3.26-3.38 (m, 1H), 3.81-3.95 (t, 1H), 4.02-4.11 (d, 1H), 4.13-4.25 (d, 1H), 6.48-6.60 (m, 2H), 7.70-6.98 (m, 1H) 7.08-7.28 (m, 5H). LCMS (12 minutes method) [M+H]$^+$=320 @ Rt 4.20 min. major peak.

EXAMPLE 21

Preparation of 2-(2,6-Dichloro-phenyl)-1-morpholin-2-yl-1-phenyl-ethanol hydrochloride a) 1-(4-Benzyl-morpholin-2-yl)-2-(2,6-dichloro-phenyl)-1-phenyl-ethanol

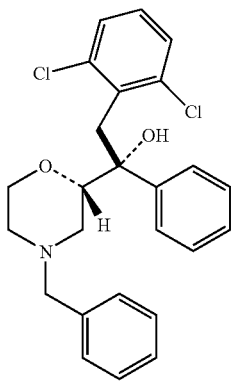

The procedure for the synthesis of example 18a, 1-(4-Benzyl-morpholin-2-yl)-2-(2-chloro-6-fluoro-phenyl)-1-phenyl-ethanol, using 2,6-dichlorobenzyl magnesium chloride as starting material (available from Rieke Metals) was followed making non-critical variations, to yield the title compound. This material was used in step b) without further purification. LCMS (6 minutes method) [M+H]$^+$=442 @ Rt 3.49 min. major peak.

b) 2-(2,6-Dichloro-phenyl)-1-morpholin-2-yl-1-phenyl-ethanol hydrochloride

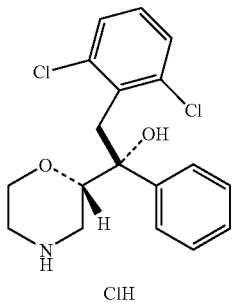

To a solution of 1-(4-Benzyl-morpholin-2-yl)-2-(2,6-dichloro-phenyl)-1-phenyl-ethanol (450 mg, 1 equiv.) in ethyl acetate (15 mL) at room temperature under nitrogen atmosphere was added ammonium formate (1.69 g, 25 equiv.) followed by addition of palladium on charcoal (10%, 45 mg.). The reaction mixture was heated to reflux for 3 hour, cooled to room temperature and then filtered through Celite. All volatiles were evaporated under vacuum, and the resulting solid was purified via preparative HPLC. The isolated white solid was taken up in ethanol. Hydrogen chloride was added (large excess of 2M solution in diethyl ether) and the mixture was stirred until it became a clear solution. Then all the volatiles were evaporated "in vacuo", to give 60 mg of the title compound as white solid. $^1$H NMR (300M$_1$, CD$_3$OD D4) δ: 2.52-2.61 (d, 1H), 2.79-2.96 (t, 1H), 2.98-3.13 (t, 1H), 3.15-3.19 (s, 1H), 3.56-3.71 (q, 2H), 3.88-4.02 (t, 1H), 4.10-4.21 (d, 1H), 4.29-4.39 (d, 1H), 6.97-7.08 (m, 1H), 7.10-7.21 (m, 7H). LCMS (12 minutes method) [M+H]$^+$=352 @ Rt 4.63 min. single major peak.

EXAMPLE 22

Preparation of 2-(2,5-Dichloro-phenyl)-1-morpholin-2-yl-1-phenyl-ethanol hydrochloride a) 1-(4-Benzyl-morpholin-2-yl)-2-(2,5-dichloro-phenyl)-1-phenyl-ethanol

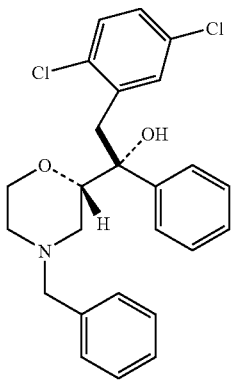

The procedure for the synthesis of example 18a, 1-(4-Benzyl-morpholin-2-yl)-2-(2-chloro-6-fluoro-phenyl)-1-phenyl-ethanol, using 2,5-dichlorobenzyl magnesium chloride as starting material (available from Rieke Metals) was followed making non-critical variations, to yield the title compound. This material was used in step b) without further purification. LCMS (6 minutes method) [M+H]$^+$=442 @ Rt 3.48 min. major peak.

b) 2-(2,5-Dichloro-phenyl)-1-morpholin-2-yl-1-phenyl-ethanol hydrochloride

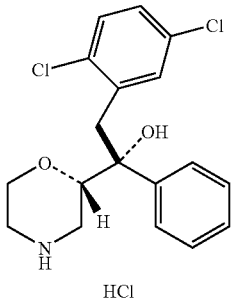

The procedure for the synthesis of example 21b, 1-(4-Benzyl-morpholin-2-yl)-2-(2,6-dichloro-phenyl)-1-phenyl-ethanol, was followed making non-critical variations to the title compound. $^1$H NMR (300 MHz, CD$_3$OD D4) δ: 2.49-2.61 (d, 1H), 2.88-3.11(m, 2H), 3.12-3.24 (m, 1H), 3.24-3.35 (m, 1H), 3.41-3.53 (d, 1H), 3.82-3.96 (m, 1H), 4.04-4.25 (m, 2H), 6.90-7.00 (m, 1H), 7.02-7.29 (m, 7H). LCMS (12 minutes method) [M+H]$^+$=352@ Rt 4.86 min. major peak

EXAMPLE 23

Preparation of 2-(2,5-Difluoro-phenyl)-1-morpholin-2-yl-1-phenyl-ethanol hydrochloride a) 1-(4-Benzyl-morpholin-2-yl)-2-(2,5-difluoro-phenyl)-1-phenyl-ethanol

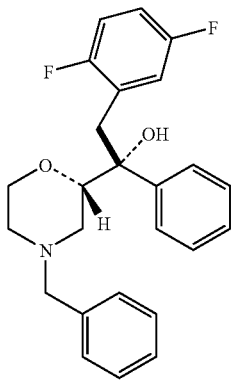

The procedure for the synthesis of example 18a, 1-(4-Benzyl-morpholin-2-yl)-2-(2-chloro-6-fluoro-phenyl)-1-phenyl-ethanol, using 2,5-difluorobenzyl magnesium bromide as starting material (available from Rieke Metals) was followed making non-critical variations, to yield the title compound. This material was used in step b) without further purification. LCMS (6 minutes method) [M+H]$^+$=410 @ Rt 3.11 min. major peak.

b) 2-(2,5-Difluoro-phenyl)-1-morpholin-2-yl-1-phenyl-ethanol hydrochloride

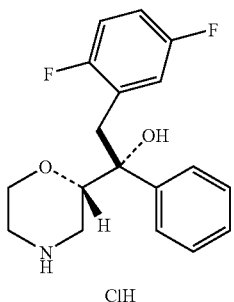

The procedure for the synthesis of example 18b, 2-(2-Fluoro-6-chloro-phenyl)-1-morpholin-2-yl-1-phenyl-ethanol hydrochloride, was followed making non-critical variations, to yield the title compound. $^1$H NMR (300 MHz, CD$_3$OD D4) δ: 2.48-2.59 (d, 1H), 2.87-3.09 (m, 2H), 3.11-3.17 (m, 1H), 3.26-3.38 (m, 2H), 3.81-3.95 (t, 1H), 4.02-4.11 (d, 1H), 4.13-4.25 (d, 1H), 6.62-6.77 (m, 3H), 7.08-7.28 (m, 5H). LCMS (12 minutes method) [M+H]$^+$=320 @ Rt 4.20 min. single major peak.

EXAMPLE 24

Preparation of 2-(2-Fluoro-5-phenyl-phenyl)-1-morpholin-2-yl-1-phenyl-ethanol hydrochloride a) 1-(4-Benzyl-morpholin-2-yl)-2-(–2-biphenyl-5-flouro-phenyl)-1-phenyl-ethanol

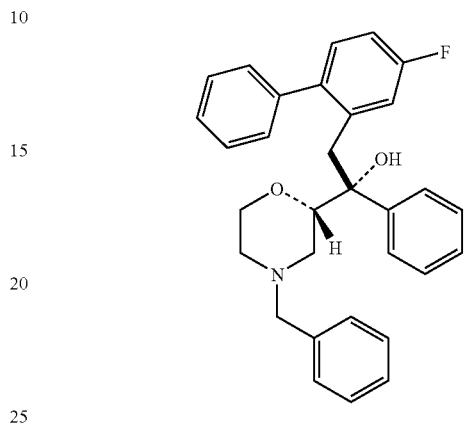

The procedure for the synthesis of example 18a, 1-(4-Benzyl-morpholin-2-yl)-2-(2-chloro-6-fluoro-phenyl)-1-phenyl-ethanol, using 2-phenyl-5-fluorobenzyl magnesium bromide as starting material was followed making non-critical variations, to yield the title compound. This material was used in step b) without further purification. LCMS (6 minutes method) [M+H]$^+$=468 @ Rt 3.62 min. major peak.

b) 2-(2-Fluoro-5-phenyl-phenyl)-1-morpholin-2-yl-1-phenyl-ethanol hydrochloride

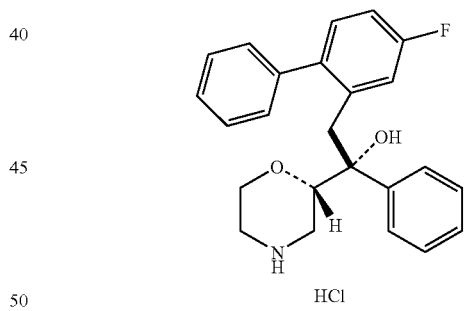

The procedure for the synthesis of example 18b, 2-(2-Fluoro-6-chloro-phenyl)-1-morpholin-2-yl-1-phenyl-ethanol hydrochloride, was followed making non-critical variations to the title compound. $^1$H NMR (300 MHz, CD$_3$OD D4) δ: 2.35-2.48 (d, 1H), 2.77-2.91 (t, 1H), 2.91-3.04 (m, 1H), 3.04-3.16 (m, 1H), 3.22-3.28 (m, 1H), 3.30-3.42 (m, 1H), 3.66-3.87 (m, 2H), 4.01-4.14 (d, 1H), 6.70-6.89 (m, 5H), 6.98-7.11 (m, 4H), 7.14-7.25 (m, 4H). LCMS (12 minutes method) [M+H]$^+$=378@ Rt 5.22 min. major peak.

Solid Phase Synthesis of Compounds of the Invention

Compounds of the invention wherein Ar$_1$ is substituted with an aromatic group (i.e. pyridyl, thiophenyl and optionally substituted phenyl) may be prepared by solid phase synthesis using the route shown below (the black dot represents polystyrene resin).

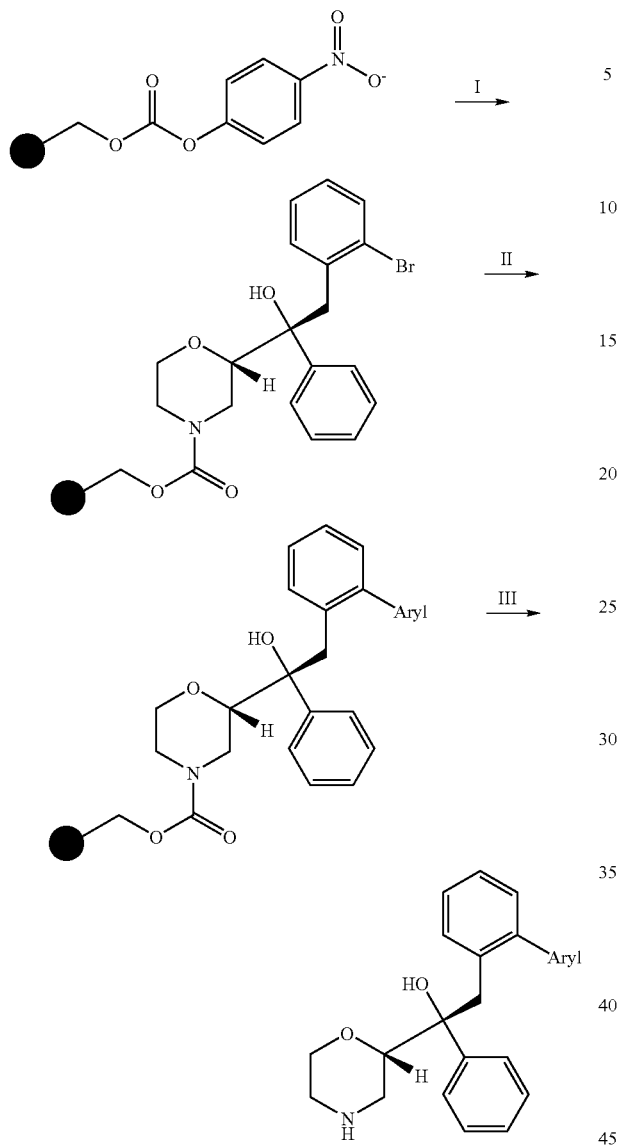

The sequence is preferably performed on a polystyrene resin, without characterisation of the resin-bound intermediates.

i) Aliquots (52 mg, 0.05 mmoles) of p-nitrophenyl carbonate resin (Novabiochem) were dispensed into 4.5 ml MiniBlock reaction tubes (Mettler-Toledo). To each resin was added DMF (0.5 ml) followed by a 0.2M solution of 2-(2-bromo-phenyl)-1-morpholin-2-yl-1-phenyl-ethanol in DMP (0.5 ml, 0.1 mmoles). The tubes were sealed and agitated by orbital shaking for 24 hrs. The resins were then filtered and washed with DMF (3×1.0 ml), a solution of diisopropylethylamine (0.25 ml) in DMF (1.0 ml) and finally DMF (4×1.0 ml).

ii) To each resin was added a 2M solution of an optionally substituted aryl boronic acid in DMF (0.5 ml, 1.0 mmoles), a 0.5M solution of triphenylphosphine in DMF (0.2 ml, 0.1 mmoles), a 0.25M solution of Pd(II) acetate in DMF (0.2 ml, 0.05 mmoles) and a 1.25M solution of caesium carbonate in water (0.1 ml, 0.125 mmoles). The tubes were sealed, agitated by orbital shaking and heated at 80° for 20 hrs. The reactions were then cooled to ambient temperature and the resins washed with DMF (2×1.0 ml), MeOH (3×1.0 ml) and DCM (4×1.0 ml).

iii) To each resin was added a TFA/H$_2$O mixture (95:5 v/v, 1 ml). The tubes were sealed and agitated by orbital shaking for 6 hrs. The reactions were filtered and washed with DCM (2×2 ml). Appropriate filtrates and washings were combined and volatile components removed by vacuum evaporation. Each residue was dissolved in MeOH (1 ml) and the solutions applied to MeOH-washed SCX-2 cartridges (0.5 g/3.0 ml) (Jones Chromatography). After draining under gravity the cartridges were washed with MeOH (2.5 ml) and the products then eluted using a 2M solution of ammonia in MeOH (2.5 ml). Removal of volatile components by vacuum evaporation gave the desired products which were purified by preparative LCMS.

By this means were prepared:

EXAMPLE 25

2-(4'-methyl-biphenyl-2-yl)-1-morpholin-2-yl-1-phenyl-ethanol, RT (6 min gradient) 3.11 min, [M+H]$^+$ 374.2

EXAMPLE 26

2-(4'-chloro-biphenyl-2-yl)-1-morpholin-2-yl-1-phenyl-ethanol, RT (6 min gradient) 3.36 min, [M+H]$^+$ 394.2

EXAMPLE 27

2-(4'-methoxy-biphenyl-2-yl)-1-morpholin-2-yl-1-phenyl-ethanol, RT (6 min gradient) 3.37 min, [M+H]$^+$ 390.2

EXAMPLE 28

2-(3'-fluoro-biphenyl-2-yl)-1-morpholin-2-yl-1-phenyl-ethanol, RT (6 min gradient) 3.39 min, [M+H]$^+$ 378.4

EXAMPLE 29

2-(3'-chloro-biphenyl-2-yl)-1-morpholin-2-yl-1-phenyl-ethanol, RT (6 min gradient) 3.53 min, [M+H]$^+$ 394.4

EXAMPLE 30

2-(3'-methoxy-biphenyl-2-yl)-1-morpholin-2-yl-1-phenyl-ethanol, RT (6 min gradient) 3.31 min, [M+H]$^+$ 390.4

EXAMPLE 31

2-(3'-methyl-biphenyl-2-yl)-1-morpholin-2-yl-1-phenyl-ethanol, RT (6 min gradient) 3.45 min, [M+H]$^+$ 374.4

EXAMPLE 32

2-(3',5'-dichloro-biphenyl-2-yl)-1-morpholin-2-yl-1-phenyl-ethanol, RT (6 min gradient) 3.71 min, [M+H]$^+$ 428.3

EXAMPLE 33

2-(2',4'-dimethyl-biphenyl-2-yl)-1-morpholin-2-yl-1-phenyl-ethanol, RT (6 min gradient) 3.59 min, [M+H]$^+$ 388.4

EXAMPLE 34

2-(2',4'-diethoxy-biphenyl-2-yl)-1-morpholin-2-yl-1-phenyl-ethanol, RT (6 min gradient) 3.33 min, [M+H]$^+$ 420.4

EXAMPLE 35

1-morpholin-2-yl-1-phenyl-2-(2-pyridin-3-yl-phenyl)-ethanol, RT (6 min gradient) 2.17 min, [M+]$^+$ 361.4

EXAMPLE 36

1-morpholin-2-yl-1-phenyl-2-(2-thiophen-3-yl-phenyl)-ethanol, 3.25 min, [M+H]$^+$ 366.4

EXAMPLE 37

2-(3',4'-dichloro-biphenyl-2-yl)-1-morpholin-2-yl-1-phenyl-ethanol, RT (6 min gradient) 3.56 min, [M+H]$^+$ 428.1

The pharmacological profile of the present compounds may be demonstrated as follows. All of the exemplified compounds above have been found to exhibit a $K_i$ value less than 500 nM at the norepinephrine transporter as determined using the scintillation proximity assay described below. Further more, all of the exemplified compounds above have been found to selectively inhibit the norepinephrine transporter relative to the serotonin and dopamine transporters by a factor of at least five using the scintillation proximity assays as described below.

Generation of Stable Cell-Lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganaphthy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™-Invitrogen) following the manufacture's protocol.

Scintillation Proximity Assays for Determining the Affinity of Test Ligands at the Norepinephrine Transporter The compounds of the present invention are norepinephrine reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus 3H-nisoxetine binding to norepinephrine re-uptake sites in a cell line transfected with DNA encoding human norepinephrine transporter binding protein has been used to determine the affinity of ligands at the norepinephrine transporter.

Membrane Preparation:

Cell pastes from large scale production of HEK-293 cells expressing cloned human norepinephrine transporters were homogenized in 4 volumes 50 mM Tris-HCl containing 300 mM NaCl and 5 mM KCl, pH 7.4. The homogenate was centrifuged twice (40,000 g, 10 min, 4° C.) with pellet re-suspension in 4 volumes of Tris-HCl buffer containing the above reagents after the first spin and 8 volumes after the second spin. The suspended homogenate was centrifuged (100 g, 10 min, 4° C.) and the supernatant kept and re-centrifuged (40,000 g, 20 min, 4° C.). The pellet was resuspended in Tris-HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[$^3$H]-Nisoxetine Binding Assay:

Each well of a 96 well microtitre plate was set up to contain the following:

50 µl 2 nM [N-methyl-3H]-Nisoxetine hydrochloride (70-87 Ci/mmol, from NEN Life Science Products)

75 µl Assay buffer (50 mM Tris-HCl pH 7.4 containing 300 mM NaCl and 5 mM KCl)

25 µl Test compound, assay buffer (total binding) or 10 µM Desipramine HCl (non-specific binding)

50 µl Wheat germ agglutinin coated poly (vinyltoluene) (WGA PVT) SPA Beads (Amersham Biosciences RPNQ0001) (10 mg/ml)

50 µl Membrane (0.2 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2458).

Membrane Preparation:

Membrane preparation is essentially similar to that for the norepinephrine transporter containing membranes as described above. The membrane preparation was stored in aliquots (1 ml) at −70° C. until required. The protein concentration of the membrane preparation was determined using a BCA protein assay reagent kit.

[³]-Citalopram Binding Assay:

Each well of a 96 well microtitre plate was set up to contain the following:

50 μl 2 nM [³H]-Citalopram (60-86 Ci/mmol, Amersham Biosciences)
75 μl Assay buffer (50 mM Tris-HCl pH 7.4 containing 150 mM NaCl and 5 mM KCl)
25 μl Diluted compound, assay buffer (total binding) or 100 μM Fluoxetine (non-specific binding)
50 μl WGA PVT SPA Beads (40 mg/ml)
50 μl Membrane preparation (0.4 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the test compounds.

Dopamine Binding Assay

The ability of a test compound to compete with [³H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[³H]-WIN35,428 Binding Assay:

Each well of a 96 well microtitre plate was set up to contain the following:

50 μl 4 nM [3H]-WIN35,428 (84-87 Ci/mmol, from NEN Life Science Products)
75 μl Assay buffer (50 mM Tris-HCl pH 7.4 containing 150 mM NaCl and 5 mM KCl)
25 μl Diluted compound, assay buffer (total binding) or 100 μM Nomifensine (non-specific binding)
50 μl WGA PVT SPA Beads (10 mg/ml)
50 μl Membrane preparation (0.2 mg protein per ml.)

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the test compounds.

Acid Stability

The acid stability of a compound according to the present invention was determined as a solution in buffer at 6 different pH values (HCl 0.1N, pH 2, pH 4, pH 6, pH 7, and pH 8) at 40° C. over a time course of 72 hours. Samples were taken at the beginning of the study and after 3, 6 and 24 hours and analysed by capillary electrophoresis. The original sample used in this study contained 0.8% of the undesired epimer as internal standard. The samples taken at the different time points during the study did not show any significant change in the percentage of the undesired epimer. This assay confirms that compounds of the present invention are chemically and configurationally stable under acidic conditions.

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the new chemical entity (NCE) was prepared in a mixture of Acetonitrile/Water to reach a final concentration of acetonitrile in the incubation below 0.5%.

The microsomal incubation mixture (total volume 0.1 mL) contained the NCE (4 μM), β-NADPH (1 mM), microsomal proteins (0.5 mg/mL), and Quinidine (0 or 2 μM) in 100 mM sodium phosphate buffer pH 7.4. The mixture was incubated for 30 minutes at 37° C. in a shaking waterbath. The reaction was terminated by the addition of acetonitrile (75 μL). The samples were vortexed and the denaturated proteins were removed by centrifugation. The amount of NCE in the supernatant was analyzed by liquid chromatography/mass spectrometry (LC/MS) after addition of an internal standard. A sample was also taken at the start of the incubation (t=0), and analysed similarly.

Analysis of the NCE was performed by liquid chromatography/mass spectrometry. Ten μL of diluted samples (20 fold dilution in the mobile phase) were injected onto a Spherisorb CN Column, 5 μM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The NCE and the internal standard were quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(NCE \text{ response in samples without inhibitor}) \text{time } 0 - (NCE \text{ response in samples without inhibitor}) \text{time } 30}{(NCE \text{ response in samples without inhibitor}) \text{time } 0} \times 100$$

The extent of metabolism with inhibitor (%) was calculated as follows:

$$\frac{(NCE \text{ response in samples without inhibitor}) \text{time } 0 - (NCE \text{ response in samples with inhibitor}) \text{time } 30}{(NCE \text{ response in samples without inhibitor}) \text{time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 µM for CYP2D6 activity, the $IC_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 µM, β-NADPH (2 mM), microsomal proteins (0.5 mg/mL), and the new chemical entity (NCE) (0, 5, and 25 µM) in 100 mM sodium phosphate buffer pH 7.4. The mixture was incubated in a shaking waterbath at 37° C. for 5 minutes. The reaction was terminated by the addition of methanol (75 µL). The samples were vortexed and the denaturated proteins were removed by centrifugation. The supernatant was analyzed by liquid chromatography connected to a fluorescence detector. The formation of the 1'-hydroxybufuralol was monitored in control samples (0 µM NCE) and in the samples incubated in presence of the NCE. The stock solution of NCE was prepared in a mixture of Acetonitrile/Water to reach a final concentration of acetonitrile in the incubation below 1.0%.

The determination of 1'hydroxybufuralol in the samples was performed by liquid chromatograhy with fluorimetric detection as described below. Twenty five µL samples were injected onto a Chromolith Performance RP-18e column (100 mm×4.6 mm) merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The $IC_{50}$ of the NCE for CYP2D6 was calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibitor})}{\text{Percent of inhibition}}$$

The $IC_{50}$ estimation is assumed valid if inhibition is between 20% and 80% (Moody G C, Griffin S J, Mather A N, McGinnity D P, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (I):

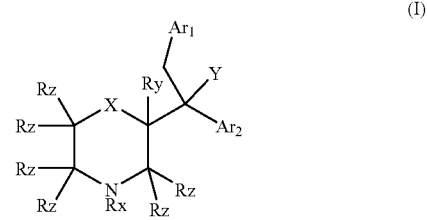

wherein:

Rx is H;

Ry is H or $C_1$-$C_4$ alkyl;

each Rz is independently H or $C_1$-$C_4$ alkyl;

X represents O;

Y represents OH or OR;

R is $C_1$-$C_4$ alkyl;

$Ar_1$ is a phenyl ring or a 5- or 6-membered heteroaryl ring, each of which can be substituted with 1, 2, 3, 4 or 5 substituents depending upon the number of available substitution positions, each independently selected from the group consisting of $C_1$-$C_4$ alkyl, O($C_1$-$C_4$ alkyl), S($C_1$-$C_4$ alkyl), halo, hydroxy, pyridyl, thiophenyl, and phenyl optionally substituted with 1, 2, 3, 4 or 5 substituents each independently selected from the group consisting of halo, $C_1$-$C_4$ alkyl, and O($C_1$-$C_4$ alkyl); and $Ar_2$ is a phenyl ring or a 5- or 6-membered heteroaryl ring, each of which can be substituted with 1, 2, 3, 4 or 5 substituents depending upon the number of available substitution positions, each independently selected from the group consisting of $C_1$-$C_4$ alkyl, O($C_1$-$C_4$ alkyl) and halo;

wherein each above-mentioned $C_1$-$C_4$ alkyl group is optionally substituted with one or more halo atoms;

or a pharmaceutically acceptable salt thereof.

2. The compound of claim 1, wherein:

$Ar_1$ is phenyl, pyridyl, pyrimidyl, thiazolyl, isothiazolyl, oxazolyl, isoxazolyl, thiophenyl, furanyl, imidazolyl, triazolyl, oxadiazolyl or thiadiazolyl, each of which can be substituted with 1, 2, 3, 4 or 5 substituents depending upon the number of available substitution positions, each independently selected from the group consisting of $C_1$-$C_4$ alkyl, O($C_1$-$C_4$ alkyl), S($C_1$-$C_4$ alkyl), halo, hydroxy, pyridyl, thiophenyl, and phenyl optionally substituted with 1, 2, 3, 4 or 5 substituents, each independently selected from the group consisting of halo, $C_1$-$C_4$ alkyl, or O($C_1$-$C_4$ alkyl); and $Ar_2$ is phenyl, pyridyl, pyrimidyl, thiazolyl, isothiazolyl, oxazolyl, isoxazolyl, thiophenyl, furanyl, imidazolyl, or triazolyl, each of which can be substituted with 1, 2, 3, 4 or 5 substituents depending upon the number of available substitution positions, each independently selected from the group consisting of $C_1$-$C_4$ alkyl, O($C_1$-$C_4$ alkyl) and halo;

wherein each above-mentioned $C_1$-$C_4$ alkyl group is optionally substituted with one or more halo atoms.

3. The compound of claim 1, wherein:

$Ar_1$ is unsubstituted phenyl or phenyl substituted with 1, 2, 3, 4 or 5 substituents each independently selected from the group consisting of $C_1$-$C_4$ alkyl, O($C_1$-$C_4$ alkyl), S($C_1$-$C_4$ alkyl), halo, and phenyl optionally substituted with halo, $C_1$-$C_4$ alkyl, or O($C_1$-$C_4$ alkyl); and $Ar_2$ is unsubstituted phenyl or phenyl substituted with 1, 2, 3, 4 or 5 substituents each independently selected from the group consisting of $C_1$-$C_4$ alkyl, O($C_1$-$C_4$ alkyl), and halo;

wherein each above-mentioned $C_1$-$C_4$ alkyl group is optionally substituted with one or more halo atoms.

4. The compound of claim 1, represented by the formula (II):

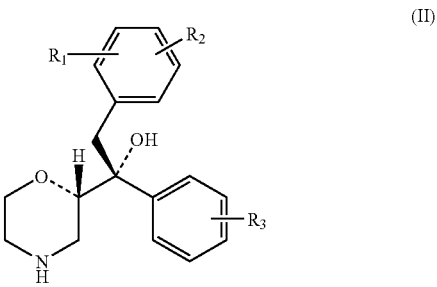

wherein $R_1$ and $R_2$ are each independently selected from the group consisting of H, $C_1$-$C_4$ alkyl, O($C_1$-$C_4$ alkyl), S($C_1$-$C_4$ alkyl), halo, and phenyl; and $R_3$ is selected from the group consisting of H, $C_1$-$C_4$ alkyl, and halo;

wherein each above-mentioned $C_1$-$C_4$ alkyl group is optionally substituted with one or more halo atoms;

or a pharmaceutically acceptable salt thereof.

5. The compound of claim 4, wherein $R_1$ is selected from the group consisting of $C_1$-$C_4$ alkyl, O($C_1$-$C_4$ alkyl), F, and Ph, wherein each above-mentioned $C_1$-$C_4$ alkyl group is optionally substituted with one or more halo atoms.

6. The compound of claim 4, wherein $R_2$ is H or F.

7. The compound of claim 4, wherein $R_3$ is H.

8. The compound of claim 1, wherein $Ar_1$ includes a substituent attached at the 2-position.

9. The compound of claim 1 of the formula:

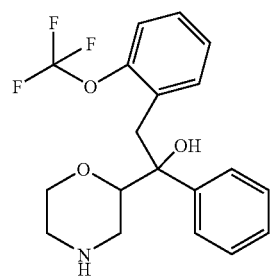

or a pharmaceutically acceptable salt thereof.

10. The compound of claim 1 of the formula:

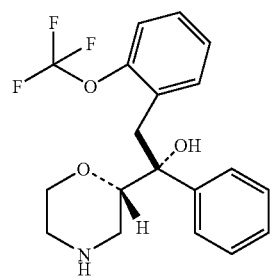

or a pharmaceutically acceptable salt thereof.

11. The compound of claim 1 of the formula:
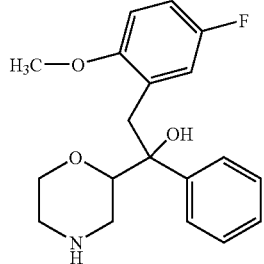
or a pharmaceutically acceptable salt thereof.
12. The compound of claim 1 of the formula:
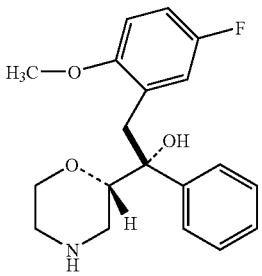
or a pharmaceutically acceptable salt thereof.
13. A pharmaceutical composition comprising a compound of claim 1, or a pharmaceutically acceptable salt thereof, together with a pharmaceutically acceptable diluent, excipient, or carrier.
* * * * *